US012168044B2

(12) United States Patent
Weinschenk et al.

(10) Patent No.: US 12,168,044 B2
(45) Date of Patent: Dec. 17, 2024

(54) PEPTIDES AND COMBINATION OF PEPTIDES FOR USE IN IMMUNOTHERAPY AGAINST NON-SMALL CELL LUNG CANCER AND OTHER CANCERS

(71) Applicant: Immatics Biotechnologies GmbH, Tuebingen (DE)

(72) Inventors: Toni Weinschenk, Tuebingen (DE); Oliver Schoor, Tuebingen (DE); Andrea Mahr, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 0 days.

(21) Appl. No.: 18/490,581

(22) Filed: Oct. 19, 2023

(65) Prior Publication Data

US 2024/0123044 A1 Apr. 18, 2024

Related U.S. Application Data

(60) Division of application No. 16/681,472, filed on Nov. 12, 2019, now abandoned, which is a continuation of application No. 15/460,396, filed on Mar. 16, 2017, now abandoned.

(60) Provisional application No. 62/308,944, filed on Mar. 16, 2016.

(30) Foreign Application Priority Data

Mar. 16, 2016 (GB) ..................... 1604458

(51) Int. Cl.
| | |
|---|---|
| *C07K 7/06* | (2006.01) |
| *A61K 35/17* | (2015.01) |
| *A61K 39/00* | (2006.01) |
| *C07K 7/08* | (2006.01) |
| *C07K 14/47* | (2006.01) |
| *C07K 14/705* | (2006.01) |
| *C07K 14/74* | (2006.01) |
| *C07K 16/28* | (2006.01) |
| *C07K 16/30* | (2006.01) |
| *C12N 5/0783* | (2010.01) |
| *C12N 15/115* | (2010.01) |
| *C12Q 1/6886* | (2018.01) |

(52) U.S. Cl.
CPC ............ *A61K 39/0011* (2013.01); *C07K 7/06* (2013.01); *C07K 7/08* (2013.01); *C07K 14/4748* (2013.01); *C07K 14/705* (2013.01); *C07K 14/70503* (2013.01); *C07K 16/2803* (2013.01); *C07K 16/2833* (2013.01); *C07K 16/30* (2013.01); *C12N 5/0638* (2013.01); *C12N 15/115* (2013.01); *C12Q 1/6886* (2013.01); *A61K 2039/5158* (2013.01); *A61K 2039/572* (2013.01); *A61K 2039/80* (2018.08); *C07K 2317/32* (2013.01); *C07K 2319/40* (2013.01); *C12N 2310/16* (2013.01); *C12Q 2600/156* (2013.01); *C12Q 2600/158* (2013.01)

(58) Field of Classification Search
CPC ........ A61K 39/0011; A61K 2039/5158; A61K 2039/572; C07K 7/06; C07K 14/4748; C12N 5/0638

See application file for complete search history.

(56) References Cited

U.S. PATENT DOCUMENTS

| | | |
|---|---|---|
| 4,179,338 A | 12/1979 | Gordon |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,861,719 A | 8/1989 | Miller |
| 4,975,278 A | 12/1990 | Senter et al. |
| 5,202,238 A | 4/1993 | Fell et al. |
| 5,204,244 A | 4/1993 | Fell et al. |
| 5,208,020 A | 5/1993 | Chari et al. |
| 5,278,056 A | 1/1994 | Bank et al. |
| 5,624,821 A | 4/1997 | Winter et al. |

(Continued)

FOREIGN PATENT DOCUMENTS

| | | |
|---|---|---|
| AU | 2003236645 B2 | 12/2003 |
| CN | 101870725 A | 10/2010 |

(Continued)

OTHER PUBLICATIONS

Jia et al., Identification of Two Novel HLA-A*0201-Restricted CTL Epitopes Derived from MAGE-A4, Clin Developmental Immun., Article ID 567594, pp. 1-7. (Year: 2010).*
Zhang et al., A MAGE-A4 peptide presented by HLA-B37 is ecognized on human tumors by cytolytic lymphocytes, Tissue Antigens, 60:365-371. (Year: 2002).*
NCT02096614 (version 3), Multi-center, Investigator Initiated Phase 1 Study of MAGE-A4 Specific TCR Gene Transferred TLymphocytes With Solid Tumors, Mar. 14, (Year: 2014).*
English translation of CN-105219714-A, Jan. 6, 2016.*

(Continued)

*Primary Examiner* — Hong Sang
(74) *Attorney, Agent, or Firm* — McBee Moore & Vanik IP, LLC

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

20 Claims, 6 Drawing Sheets

Specification includes a Sequence Listing.

(56) References Cited

U.S. PATENT DOCUMENTS

| | | | |
|---|---|---|---|
| 5,731,168 A | 3/1998 | Carter et al. | |
| 5,807,706 A | 9/1998 | Carter et al. | |
| 5,821,333 A | 10/1998 | Carter et al. | |
| 5,882,877 A | 3/1999 | Gregory et al. | |
| 6,013,516 A | 1/2000 | Verma et al. | |
| 6,018,032 A | 1/2000 | Koike et al. | |
| 6,127,175 A | 10/2000 | Vigne et al. | |
| 6,464,998 B1 | 10/2002 | Beuzard et al. | |
| 6,805,861 B2 | 10/2004 | Stauss | |
| 7,429,652 B2 | 9/2008 | Wang et al. | |
| 7,642,228 B2 | 1/2010 | Carter et al. | |
| 7,695,936 B2 | 4/2010 | Carter et al. | |
| 7,807,392 B1 | 10/2010 | Domon et al. | |
| 7,807,642 B2 | 10/2010 | Dengjel | |
| 7,811,828 B2 | 10/2010 | Lemmel et al. | |
| 7,833,969 B2 | 11/2010 | Dengjel | |
| 7,833,970 B2 | 11/2010 | Dengjel | |
| 8,080,634 B2 | 12/2011 | Singh et al. | |
| 8,216,805 B2 | 7/2012 | Carter et al. | |
| 8,323,657 B2 | 12/2012 | Nishimura | |
| 8,647,629 B2 | 2/2014 | Rammensee et al. | |
| 8,669,230 B2 | 3/2014 | Singh et al. | |
| 9,498,512 B2 | 11/2016 | Rammensee et al. | |
| 9,511,128 B2 | 12/2016 | Singh et al. | |
| 9,688,762 B2 | 6/2017 | Igawa et al. | |
| 9,791,443 B2 | 10/2017 | Weinschenk et al. | |
| 9,791,444 B2 | 10/2017 | Weinschenk et al. | |
| 9,943,579 B2 | 4/2018 | Weinschenk et al. | |
| 9,950,048 B2 | 4/2018 | Singh et al. | |
| 10,064,924 B2 | 9/2018 | Rammensee et al. | |
| 10,071,148 B2 | 9/2018 | Weinschenk et al. | |
| 10,106,805 B2 | 10/2018 | Spangenberg et al. | |
| 10,196,432 B2 | 2/2019 | Dengjel | |
| 10,286,052 B2 | 5/2019 | Rammensee et al. | |
| 10,420,800 B2 | 9/2019 | Weinschenk et al. | |
| 10,434,136 B2 | 10/2019 | Rammensee et al. | |
| 10,538,573 B2 | 1/2020 | Maurer et al. | |
| 10,618,945 B2 | 4/2020 | Dengjel | |
| 10,626,160 B2* | 4/2020 | Maurer | C07K 14/7051 |
| 10,683,495 B2 | 6/2020 | Bunk et al. | |
| 10,889,629 B2* | 1/2021 | Maurer | C07K 14/7051 |
| 10,946,064 B2 | 3/2021 | Kuttruff-Coqui et al. | |
| 11,028,142 B2 | 6/2021 | Baeuerle et al. | |
| 11,072,645 B2 | 7/2021 | Bunk et al. | |
| 11,104,894 B2 | 8/2021 | Bunk et al. | |
| 11,464,800 B2 | 10/2022 | Kalra et al. | |
| 11,524,059 B2 | 12/2022 | Kuttruff-Coqui et al. | |
| 11,529,400 B1 | 12/2022 | Kuttruff-Coqui et al. | |
| 11,529,401 B2 | 12/2022 | Kuttruff-Coqui et al. | |
| 11,542,059 B2 | 1/2023 | Collis et al. | |
| 11,607,446 B2 | 3/2023 | Kuttruff-Coqui et al. | |
| 11,759,507 B2 | 9/2023 | Kuttruff-Coqui et al. | |
| 11,890,333 B2 | 2/2024 | Kuttruff-Coqui et al. | |
| 11,890,334 B2 | 2/2024 | Kuttruff-Coqui et al. | |
| 2005/0063947 A1 | 3/2005 | Hwu et al. | |
| 2008/0038285 A1 | 2/2008 | Lemmel et al. | |
| 2008/0206216 A1 | 8/2008 | Dengjel | |
| 2009/0060910 A1 | 3/2009 | Johnson et al. | |
| 2009/0136528 A1 | 5/2009 | Singh et al. | |
| 2010/0029571 A1 | 2/2010 | Rammensee et al. | |
| 2010/0034841 A1 | 2/2010 | Nishimura et al. | |
| 2010/0040641 A1* | 2/2010 | Tsunoda | A61K 39/0011 435/375 |
| 2011/0027266 A1 | 2/2011 | Lee et al. | |
| 2011/0070208 A1 | 3/2011 | Bertoletti et al. | |
| 2011/0117117 A1 | 5/2011 | Singh et al. | |
| 2011/0189141 A1 | 8/2011 | Kieback et al. | |
| 2011/0229504 A1* | 9/2011 | Fritsche | A61K 38/4886 435/69.3 |
| 2011/0257890 A1 | 10/2011 | Weinschenk et al. | |
| 2011/0318380 A1 | 12/2011 | Brix et al. | |
| 2013/0058909 A1 | 3/2013 | Szabolcs et al. | |
| 2013/0096016 A1 | 4/2013 | Weinschenk et al. | |
| 2013/0273647 A1 | 10/2013 | Sahin et al. | |
| 2013/0323272 A1 | 12/2013 | Rammensee et al. | |
| 2014/0086943 A1 | 3/2014 | Weinschenk et al. | |
| 2014/0127242 A1 | 5/2014 | Rammensee et al. | |
| 2014/0271692 A1 | 9/2014 | Singh et al. | |
| 2015/0125477 A1 | 5/2015 | Kuttruff-Coqui et al. | |
| 2015/0166661 A1 | 6/2015 | Chen et al. | |
| 2015/0320848 A1 | 11/2015 | Rammensee et al. | |
| 2015/0337369 A1 | 11/2015 | Davis et al. | |
| 2016/0017038 A1 | 1/2016 | Koenig | |
| 2016/0051654 A1 | 2/2016 | Singh et al. | |
| 2016/0168200 A1 | 6/2016 | Weinschenk et al. | |
| 2016/0187351 A1 | 6/2016 | Weinschenk et al. | |
| 2016/0279215 A1 | 9/2016 | Mahr et al. | |
| 2017/0202937 A1 | 7/2017 | Weinschenk et al. | |
| 2017/0267738 A1 | 9/2017 | Maurer et al. | |
| 2017/0296641 A1 | 10/2017 | Weinschenk et al. | |
| 2017/0319675 A1 | 11/2017 | Weinschenk et al. | |
| 2017/0342154 A1 | 11/2017 | Igawa et al. | |
| 2018/0135039 A1 | 5/2018 | Bunk et al. | |
| 2018/0162922 A1 | 6/2018 | Bunk et al. | |
| 2018/0208657 A1 | 7/2018 | Jung et al. | |
| 2018/0311330 A1 | 11/2018 | Rammensee et al. | |
| 2019/0016801 A1 | 1/2019 | Hofmann et al. | |
| 2019/0016802 A1 | 1/2019 | Hofmann et al. | |
| 2019/0016803 A1 | 1/2019 | Hofmann et al. | |
| 2019/0016804 A1 | 1/2019 | Hofmann et al. | |
| 2019/0040378 A1 | 2/2019 | Fotin-Mleczek et al. | |
| 2019/0076476 A1 | 3/2019 | Weinschenk et al. | |
| 2019/0175650 A1 | 6/2019 | Dao et al. | |
| 2019/0185539 A1 | 6/2019 | Ogasawara | |
| 2019/0192691 A1 | 6/2019 | Barrett et al. | |
| 2019/0201443 A1 | 7/2019 | Joglekar et al. | |
| 2019/0216852 A1 | 7/2019 | Kalra et al. | |
| 2019/0256571 A1 | 8/2019 | Baeuerle et al. | |
| 2019/0292520 A1 | 9/2019 | Alpert | |
| 2019/0309042 A1 | 10/2019 | Maurer et al. | |
| 2019/0336531 A1 | 11/2019 | Stauss et al. | |
| 2019/0338012 A1 | 11/2019 | Stauss et al. | |
| 2020/0078439 A1 | 3/2020 | Rammensee et al. | |
| 2020/0085930 A1 | 3/2020 | Weinschenk et al. | |
| 2020/0263162 A1 | 8/2020 | Bunk et al. | |
| 2020/0354676 A1 | 11/2020 | Gu | |
| 2021/0041435 A1 | 2/2021 | Ogasawara | |
| 2021/0228697 A1 | 7/2021 | Kuttruff-Coqui et al. | |
| 2021/0238543 A1 | 8/2021 | Renes et al. | |
| 2021/0355478 A1 | 11/2021 | Bunk et al. | |
| 2021/0369826 A1 | 12/2021 | Kuttruff-Coqui et al. | |
| 2021/0380659 A1 | 12/2021 | Bunk et al. | |
| 2021/0393754 A1 | 12/2021 | Kuttruff-Coqui et al. | |
| 2022/0080030 A1 | 3/2022 | Johnson et al. | |
| 2022/0119479 A1 | 4/2022 | Conroy et al. | |
| 2022/0185888 A1 | 6/2022 | Hofmann et al. | |
| 2022/0195044 A1 | 6/2022 | Hofmann et al. | |
| 2022/0267406 A1 | 8/2022 | Stauss et al. | |
| 2022/0356252 A1 | 11/2022 | Bunk et al. | |
| 2022/0362362 A1 | 11/2022 | Kuttruff-Coqui et al. | |
| 2022/0362363 A1 | 11/2022 | Kuttruff-Coqui et al. | |
| 2023/0089882 A1 | 3/2023 | Kuttruff-Coqui et al. | |
| 2023/0263873 A1 | 8/2023 | Kuttruff-Coqui et al. | |

FOREIGN PATENT DOCUMENTS

| | | | |
|---|---|---|---|
| CN | 101870725 B | | 6/2012 |
| CN | 105219714 A | | 1/2016 |
| CN | 105219719 A | * | 1/2016 |
| EP | 1194542 A1 | | 4/2002 |
| EP | 1306431 A1 | | 8/2004 |
| EP | 1859266 A2 | | 11/2007 |
| EP | 1760088 B1 | | 3/2008 |
| EP | 1930433 A1 | | 6/2008 |
| EP | 2119726 A1 | | 11/2009 |
| EP | 2258719 A1 | | 12/2010 |
| EP | 2322543 A1 | | 5/2011 |
| EP | 2337795 A2 | | 6/2011 |
| EP | 2660250 A1 | | 11/2013 |
| EP | 2752198 A1 | | 7/2014 |
| EP | 2897981 A1 | | 7/2015 |
| EP | 2970484 A1 | | 1/2016 |
| EP | 3015477 A1 | | 5/2016 |
| EP | 3286210 A1 | | 2/2018 |

(56) References Cited

FOREIGN PATENT DOCUMENTS

| | | |
|---|---|---|
| EP | 3443001 A1 | 2/2019 |
| EP | 3494138 A1 | 6/2019 |
| EP | 3494984 A1 | 6/2019 |
| EP | 3529267 A1 | 8/2019 |
| EP | 3529352 A2 | 8/2019 |
| EP | 3668539 A1 | 6/2020 |
| EP | 3770168 A1 | 1/2021 |
| EP | 3802614 A1 | 4/2021 |
| EP | 3886872 A1 | 10/2021 |
| EP | 3911298 A1 | 11/2021 |
| EP | 3917955 A1 | 12/2021 |
| JP | 2013126415 A | 6/2013 |
| TW | I764886 B | 5/2022 |
| WO | 8101145 A1 | 4/1981 |
| WO | 8705330 A1 | 9/1987 |
| WO | 8807378 A1 | 10/1988 |
| WO | 9411026 A1 | 5/1994 |
| WO | 9419478 A1 | 9/1994 |
| WO | 9514785 A1 | 6/1995 |
| WO | 9622378 A1 | 7/1996 |
| WO | 9710354 A1 | 3/1997 |
| WO | 0052163 A1 | 9/2000 |
| WO | 0141741 A1 | 6/2001 |
| WO | 200148145 A2 | 7/2001 |
| WO | 02072627 A2 | 9/2002 |
| WO | 2003100432 A1 | 12/2003 |
| WO | 2004044004 A2 | 5/2004 |
| WO | 2004091668 A1 | 10/2004 |
| WO | 2005076009 A1 | 8/2005 |
| WO | 2006091734 A2 | 8/2006 |
| WO | 2007028574 A2 | 3/2007 |
| WO | 2007032255 A1 | 3/2007 |
| WO | 2008053579 A1 | 5/2008 |
| WO | 2009015842 A2 | 2/2009 |
| WO | 2009032661 A1 | 3/2009 |
| WO | 2010037395 A2 | 4/2010 |
| WO | 2011039507 A1 | 4/2011 |
| WO | 2011044186 A1 | 4/2011 |
| WO | 2011066265 A1 | 6/2011 |
| WO | 2011128448 A1 | 10/2011 |
| WO | 2012135345 A1 | 10/2012 |
| WO | 2013026837 A1 | 2/2013 |
| WO | 2013057596 A1 | 4/2013 |
| WO | 2014018863 A1 | 1/2014 |
| WO | 2014043441 A1 | 3/2014 |
| WO | 2014083173 A1 | 6/2014 |
| WO | 2014153470 A2 | 9/2014 |
| WO | 2014159940 A1 | 10/2014 |
| WO | 2015018805 A1 | 2/2015 |
| WO | 2015063302 A2 | 5/2015 |
| WO | 2015075939 A1 | 5/2015 |
| WO | 2015169945 A2 | 11/2015 |
| WO | 2015172843 A1 | 11/2015 |
| WO | WO-2016053339 A1 * | 4/2016 ......... A61K 39/0011 |
| WO | 2016071343 A1 | 5/2016 |
| WO | 2016107740 A1 | 7/2016 |
| WO | 2016116626 A1 | 7/2016 |
| WO | 2016146505 A1 | 9/2016 |
| WO | 2016184592 A1 | 11/2016 |
| WO | 2017070608 A1 | 4/2017 |
| WO | 2017109496 A1 | 6/2017 |
| WO | 2017157972 A1 | 9/2017 |
| WO | 2017158103 A1 | 9/2017 |
| WO | 2018091396 A1 | 5/2018 |
| WO | 2018104407 A1 | 6/2018 |
| WO | 2019008001 A1 | 1/2019 |
| WO | 2019012138 A1 | 1/2019 |
| WO | 2019036688 A1 | 2/2019 |
| WO | 2019133853 A1 | 7/2019 |
| WO | 2019197567 A1 | 7/2019 |
| WO | 2019219709 A1 | 11/2019 |
| WO | 2019222760 A1 | 11/2019 |
| WO | 2019226941 A1 | 11/2019 |
| WO | 2019235915 A1 | 12/2019 |
| WO | 2020109616 A1 | 6/2020 |
| WO | 2020148372 A1 | 7/2020 |
| WO | 2020157211 A1 | 8/2020 |
| WO | 2020227483 A1 | 11/2020 |
| WO | 2020236795 A1 | 11/2020 |
| WO | 2020257288 A2 | 12/2020 |
| WO | 2021073624 A1 | 4/2021 |

OTHER PUBLICATIONS

Beatty, Gregory L., et al. "IFN-g-Dependent Inhibition of Tumor Angiogenesis by Tumor-Infiltrating CD41 T Cells Requires Tumor Responsiveness to IFN-y1" Journal of Immunology, vol. 166, No. 4, pp. 2276-2282, Feb. 15, 2001.

Boon, Thierry, et al. "Human tumor antigens recognized by T lymphocytes" Journal Exp Medicine, vol. 183, No. 3, pp. 725-729, Mar. 1996.

Braumueller, Heidi, et al. "T-helper-1-cell cytokines drive cancer into senescence" Nature, vol. 494, pp. 361-365, Feb. 2013.

Brichard, Vincent, et al. "The tyrosinase gene codes for an antigen recognized by autologous cytolytic T lymphocytes on HLA-A2 melanomas" Journal Exp Medicine, vol. 178, No. 2, pp. 489-495, Aug. 1993.

Brossart, Peter and Bevan, Michael J. "Presentation of Exogenous Protein Antigens on Major Histocompatability Complex Class I Molecules by Dendritic Cells: Pathway of Presentation and Regulation by Cytokines" Blood, vol. 90, No. 4, pp. 1594-1599, Aug. 15, 1997.

Butterfield, L.H., et al. "Generation of human T-cell responses to an HLA-A2.1-restricted peptide epitope derived from alpha-fetoprotein" Cancer Research, vol. 59, No. 12, 3134-3142, Jul. 1999.

Chen, Yao-Tseng, "A testicular antigen aberrantly expressed in human cancers detected by autologous antibody screening" Proc National Academy of Science, vol. 94, No. 5, pp. 1914-1918, Mar. 1997.

Dengjel, Jorn, et al. "Unexpected Abundance of HLA Class II Presented Peptides in Primary Renal Cell Carcinomas" Clinical Cancer Research, vol. 12, No. 14, Jul. 15, 2006.

Fujie, T., et al. "A MAGE-1-encoded HLA-A24-binding synthetic peptide induces specific anti-tumor cytotoxic T lymphocytes" International Journal of Cancer, vol. 80, No. 2, pp. 169-172, Jan. 1999.

Gazdar, A. F., "The molecular and cellular basis of human lung cancer" Anticancer Research, vol. 14, No. 1B, pp. 261-267, Jan.-Feb. 1994 (Abstract Only).

Gnjatic, Sacha, et al. "Survey of naturally occurring CD4+ T cell responses against NY-ESO-1 in cancer patients: Correlation with antibody responses" PNAS, vol. 100, No. 15, pp. 8862-8867, Jul. 22, 2003.

Harris, Curtis C. "Structure and function of the p53 tumor suppressor gene: clues for rational cancer therapeutic strategies" Journal National Cancer Institute, vol. 88, No. 20, pp. 1442-1455, Oct. 1996.

Hu, Xueyou et al. "Enhancement of cytolytic T lymphocyte precursor frequency in melanoma patients following immunization with the MAGE-1 peptide loaded antigen presenting cell-based vaccine" Cancer Research, vol. 56, No. 11, 2479-83, Jun. 1996.

Hwang, Melissa L., et al. "Cognate memory CD4+ T cells generated with dendritic cell priming influence the expansion, trafficking, and differentiation of secondary CD8+ T cells and enhance tumor control" Journal of Immunology, vol. 179, No. 9, pp. 5829-5838, Nov. 2007.

International Search Report for PCT/EP2017/056049, dated Jun. 23, 2017.

Jia et al, "Identification of Two Novel HLA-A*0201-Restrieted CTL Epitopes Derived from MAGE-A4", Clinical and Developmental Immunology, vol. 2010, pp. 1-7.

Kawakami, Yutaka, et al. "Identification of the immunodominant peptides of the MART-1 human melanoma antigen recognized by the majority of HLA-A2-restricted tumor infiltrating lymphocytes" Journal Exp Medicine, vol. 180, No. 1, pp. 347-352, Jul. 1994.

Kelly, Karen, et al. "Randomized phase III trial of paclitaxel plus carboplatin versus vinorelbine plus cisplatin in the treatment of

(56) References Cited

OTHER PUBLICATIONS patients with advanced non—small-cell lung cancer: a Southwest Oncology Group trial" Journal of Clinical Oncology, vol. 19, No. 13, pp. 3210-3218, Jul. 2001.
Kikuchi, M., et al. "Identification of a SART-1-derived peptide capable of inducing HLA-A24-restricted and tumor-specific cytotoxic T lymphocytes" International Journal of Cancer, vol. 81, No. 3, pp. 459-466, May 1999.
Mortara, Lorenzo, et al. "CIITA-Induced MHC Class II Expression in Mammary Adenocarcinoma Leads to a Th1Polarization of the Tumor Microenvironment, Tumor Rejection, and Specific Antitumor Memory" Clinical Cancer Research, vol. 12, No. 11, pp. 3435-3443, Jun. 1, 2006.
Mukherji, Bijay, et al. "Induction of antigen-specific cytolytic T cells in situ in human melanoma by immunization with synthetic peptide-pulsed autologous antigen presenting cells" Proc National Acad Science, USA, vol. 92, No. 17, pp. 8078-8082, Aug. 1995.
Mumberg, Dominik, et al. "CD41 T cells eliminate MHC class II—negative cancer cells in vivo by indirect effects of IFN-y" Immunology, vol. 96, pp. 8633-8638, Jul. 1999.
Niklinska, W., et al. "Detection of P53 abnormalities in non-small cell lung cancer by yeast functional assay" Folia Histochem Cytobiology vol. 39, No. 2, pp. 147-148, 2001 (Abstract Only).
Oiso, M., et al. "A newly identified MAGE-3-derived epitope recognized by HLA-A24-restricted cytotoxic T lymphocytes" International Journal of Cancer vol. 81, No. 3, pp. 387-394, May 1999.
Rock, K.L., et al. "Presentation of exogenous antigen with class I major histocompatibility complex molecules" Science, vol. 249, No. 4971, pp. 918-921, Aug. 1990.
Rosenberg, Steven A., et al. "Immunologic and therapeutic evaluation of a synthetic peptide vaccine for the treatment of patients with metastatic melanoma" Nature Medicine, vol. 4, No. 3, pp. 321-327, Mar. 1998.
Saito, Takuro, et al. "High expression of MAGE-A4 and MHC class I antigens in tumor cells and induction of MAGE-A4 immune responses are prognostic markers of CHP-MAGE-A4 cancer vaccine" Vaccine, vol. 32, pp. 5901-5907, 2014.
Schiller, Joan H., et al. "Comparison of four chemotherapy regimens for advanced non-small-cell lung cancer" New England Journal of Medicine, vol. 346, No. 2, pp. 92-98, Jan. 2002.
Search Report of GB1604458.8 dated Dec. 16, 2016.
Shichijo, Shigeki, et al. "A gene encoding antigenic peptides of human squamous cell carcinoma recognized by cytotoxic T lymphocytes" Journal Exp Medicine, vol. 187, No. 3, pp. 277-288, Feb. 1998.
Singh-Jasuja, Harpreet et al. "!The Tuebingen approach: identification, selection, and validation of tumor-associated HLA peptides for cancer therapy" Cancer Immunology, Immunotherapy, vol. 53, pp. 187-185, Jan. 2004.
Sozzi, Gabriella. "Molecular biology of lung cancer" European Journal of Cancer, vol. 37, Supplement 7, pp. 63-73, Oct. 2001.
Tanaka, F., et al. "Induction of antitumor cytotoxic T lymphocytes with a MAGE-3-encoded synthetic peptide presented by human leukocytes antigen-a24" Cancer Research, vol. 57, No. 20, pp. 4465-4468, Oct. 1997.
Tran, Eric, et al. "Cancer Immunotherapy Based on Mutation-Specific CD4+ T Cells in a Patient with Epithelial Cancer" Science, vol. 344, No. 6184, pp. 641-645, May 2014.
Van Der Bruggen, P., et al. "A gene encoding an antigen recognized by cytolytic T lymphocytes on a human melanoma" Science, vol. 254, No. 5038, pp. 1643-1647, Dec. 1991.
Van Der Burg, Sjoerd H., et al. "Immunogenicity of peptides bound to MHC class I molecules depends on the MHC-peptide complex stability" Journal of Immunology, vol. 156, No. 9, pp. 3308-3314, May 1996.
Vissers, Joost L., et al. "The renal cell carcinoma-associated antigen G250 encodes a human leukocyte antigen (HLA)-A2.1-restricted epitope recognized by cytotoxic T lymphocytes" Cancer Research, vol. 59, No. 21, pp. 5554-5559, Nov. 1999.

Wu et al, "Identification of a Novel CD8+ T Cell Epitope Derived from Cancer-Testis Antigen MAGE-4 in Oesophageal Carcinoma", Scandinavian Journal of Immunology, vol. 74, 2011, pp. 561-567.
Aggen, David H., et al. "Identification and engineering of human variable regions that allow expression of stable single-chain T cell receptors" Protein Engineering, Design & Selection, vol. 24, No. 4, pp. 361-372, Apr. 2011.
Aleksic, Milos, et al. "Different affinity windows for virus and cancer-specific T-cell receptors: implications for therapeutic strategies" European Journal of Immunology, vol. 42, No. 12, pp. 3174-3179, Dec. 2012.
Almagro, Juan C., et al. "Humanization of antibodies" Frontiers in Bioscience, vol. 13, pp. 1619-1633, Jan. 1, 2008.
Altschul, Stephen F., et al. "Gapped BLAST and PSI-BLAST: a new generation of protein database search programs" Nucleic Acids Research, vol. 25, No. 17, pp. 3389-3402, 1997.
Atwell, John L., et al. "Design and Expression of a Stable Bispecific scFv Dimer with Affinity for Both Glycophorin and N9 Neuraminidase" Molecular Immunology, vol. 33, No. 17/18, pp. 1301-1312, 1996. Abstract provided.
Bell, Jr., Anthony, J et al. "RD114 envelope proteins provide an effective and versatile approach to pseudotype lentiviral vectors" Experimental Biology and Medicine, vol. 235, pp. 1269-1276, 2010.
Bendig, Mary M. "Humanization of rodent monoclonal antibodies by CDR Grafting" Methods: A Companion to Methods in Enzymology, vol. 8, pp. 83-93, 1995.
Bendle, Gavin M., et al. "Preclinical development of T cell receptor gene therapy" Current Opinion in Immunology, vol. 21, Issue 2, pp. 209-214, Apr. 2009.
BioLegend (OKT3, purified anti-human CD3 antibody, Jun. 12, 2013, 3 pages).
Boder, Eric T., et al. "Yeast Surface Display for Directed Evolution of Protein Expression, Affinity, and Stability" Methods in Enzymology, vol. 328, Article 25, pp. 430-444, 2000. Abstract provided.
Bolotin et al., "Next generation sequencing for TCR repertoire profiling: Platform-specific features and correction algorithms," Eur. J. Immunol., (2012), vol. 42: 3073-3083.
Bossi et al., "Examining the presentation of tumor-associated antigens on peptide-pulsed T2 cells," OncoImmunology, (2003), vol. 2:11, e26840.
Brady, Ged, et al. "New cosmid vectors developed for eukaryotic DNA cloning" Gene, vol. 27, No. 2, pp. 223-232, Feb. 1984. Abstract provided.
Bridgeman, John S., et al. "Structural and biophysical determinants of alpha beta T-cell antigen recognition" Immunology, vol. 135, No. 1, pp. 9-18, Jan. 2012.
Brinkmann, Ulrich, et al. "The making of bispecific antibodies" mAbs, vol. 9, No. 2, pp. 182-212, Feb./Mar. 2017.
Brown, McKay, et al. "Tolerance to single, but not multiple, amino acid replacements in antibody V-H CDR2: A means of minimizing B cell wastage from somatic hypermutation?" The Journal of Immunology, vol. 156, No. 9, pp. 3285-3291, Jan. 1996.
Bunk, Sebastian, et al. "Abstract 2789: Development of highly potent T-cell receptorbispecifics with picomolar activity against tumor-specificHLA ligands" Cancer Research, vol. 78, Supplement 13, 2018 (Abstract Only).
Bunk, Sebastian, et al. "Effective Targeting of PRAME-Positive Tumors with Bispecific TCell-Engaging Receptor (TCER®) Molecules" Blood, vol. 134, Supplement 1, pp. 3368, Nov. 2019.
Burrows, Scott R., et al. "Hard wiring of T cell receptor specificity for the major histocompatibility complex is underpinned by TCR adaptability" PNAS, vol. 107, No. 23, pp. 10608-10613, Jun. 8, 2010.
Cameron, Brian J. et al., "Identification of a Titin-Derived HLA-A1-Presented Peptide as a Cross-Reactive Target for Engineered MAGE A3-Directed T Cells", Science Translational Medicine, Aug. 7, 2013, pp. 197-103, vol. 5.
Caron, Philip C., et al. "Engineered humanized dimeric forms of IgG are more effective antibodies" The Journal of experimental medicine, vol. 176, No. 4, pp. 1191-1195, Oct. 1992.
Carter, P. "Bispecific human IgG by design" Journal Immunol Methods, vol. 248, Issue 1-2, pp. 7-15, Feb. 2001.

(56) References Cited

OTHER PUBLICATIONS

Casset, Florence, et al. "A peptide mimetic of an anti-CD4 monoclonal antibody by rational design" Biochemical and Biophysical Research Communications, vol. 307, pp. 198-205, Jul. 2003.

Chang, Hsiu-Ching, et al. "A general method for facilitating heterodimeric pairing between two proteins: Application to expression of alpha and beta T-cell receptor extracellular segments" Proceedings of National Academy of Science, vol. 91, No. 24, pp. 11408-11412, Nov. 1994.

Chervin, Adam S. "Engineering higher affinity T cell receptors using a T cell display system" Journal Immunology Methods, vol. 339, No. 2, pp. 175-184, Dec. 31, 2008.

Cochlovius, Bjorn, et al. "Cure of Burkitt's lymphoma in severe combined immunodeficiency mice by T cells, tetravalent CD3xCD19 tandem diabody, and CD28 costimulation" Cancer research, vol. 60, No. 16, pp. 4336-4341, Aug. 2000.

Colman, P.S. "Effects of amino acid sequence changes on antibody-antigen interactions" Research in Immunology, vol. 145, pp. 33-36, Jan. 1994.

Craig, Ryan B., et al. "Anti-HIV Double Variable Domain Immunoglobulins Binding Both gp41 and gp120 for Targeted Delivery of Immunoconjugates" PLOS One, vol. 7, Issue 10, paper e46778, Oct. 2012.

Database UniProt [Online], Nov. 1, 1995 (Nov. 1, 1995). UniProt: P43358. Database Accession No. P43358 sequence. XP055374176.

Denardo, David G., et al."Anti-HLA-DR/anti-DOTA Diabody Construction in a Modular Gene Design Platform: Bispecific Antibodies for Pretargeted Radioimmunotherapy" Cancer Biotherapy & Radiopharmaceuticals, vol. 16, No. 6, pp. 525-535, Dec. 2001. Abstract provided.

Dennis, Mark S., et al. "Albumin Binding as a General Strategy for Improving the Pharmacokinetics of Proteins*" The Journal of Biological Chemistry, vol. 277, No. 38, pp. 35035-35043, Sep. 2002.

Dozier, Jonathan K., et al. "Site-Specific PEGylation of Therapeutic Proteins" International Journal of Molecular Sciences, vol. 16, pp. 25831-25864, Oct. 2015.

Dunbar, James, et al. "Examining Variable Domain Orientations in Antigen Receptors Gives Insight into TCR-Like Antibody Design" PLOS Computational Biology, vol. 10, Issue 9, e1003852, Sep. 2014.

Edelman, Gerald M., et al. The Covalent Structure of an Entire yG Immunoglobulin Molecule* Proceedings of the National Academy of Sciences, vol. 63, No. 1, pp. 78-85, May 1969.

Edge, Albert S. B., et al. "Deglycosylation of Glycoproteins by Trifluoromethanesulfonic Acid" Analytical Biochemistry, vol. 118, pp. 131-137, 1981.

Folch, Geraldine, et al. "The Human T cell Receptor Beta Variable (TRBV) Genes" Experimental and Clinical Immunogenetics, vol. 17, No. 1, pp. 42-54, 2000.

Freeman et al., "Profiling the T-cell receptor beta-chain repertoire by massively parallel sequencing," Genome Research, (2009), vol. 19: 1817-1824.

Ganju, et al, "Similarity between fluorescein-specific T-cell receptor and antibody in chemical details of antigen recognition," Proceedings of the National Academy of Sciences of the United States of America, (1992), vol. 89: 11552-11556.

Garcia et al., "How the T Cell Receptor Sees Antigen—A Structural View," Cell, (2005), vol. 122: 333-336.

Gattioni, Luca, et al. "Adoptive immunotherapy for cancer: building on success" National Review of Immunology, vol. 6, No. 5, pp. 383-393, May 2006.

Gillies, Stephen D., et al. "Expression of cloned immunoglobulin genes introduced into mouse L cells" Nucleic Acids Research, vol. 11, No. 22, pp. 7981-7997, Nov. 1983.

Goyarts et al., "Point mutations in the B chain CDR3 can alter the T cell receptor recognition pattern on an MHC class I/peptide complex over a broad interface area," Mol Immunol., (1998), vol. 35: 593-607.

Guo, Haiwei, et al. "Protein tolerance to random amino acid change" PNAS, vol. 101, No. 25, pp. 9205-9210, Jun. 22, 2004.

Hickman, Emma S., et al. "Antigen Selection for Enhanced Affinity T-Cell Receptor-Based Cancer Therapies" Journal of Biomolecular Screening, vol. 21, Issue 8, pp. 769-785, Sep. 2016.

Holliger, Philipp, et al. "Specific killing of lymphoma cells by cytotoxic T-cells mediated by a bispecific diabody" Protein Engineering, vol. 9, No. 3, pp. 299-305, Mar. 1996.

Hu, Hongmin, "Prediction and identification of HLA-A2/A3 restricted CTL epitopes derived from MAGE-4," (2008).

Hudecz, Ferenc. "Synthesis of Peptide Bioconjugates" Methods in Molecular Biology, vol. 298, pp. 209-223, 2005.

International Preliminary Report on Patentability from PCT/EP2018/069151, dated Jan. 14, 2020, 9 pages.

International Preliminary Report on Patentability from PCT/EP2018/069157, dated Jan. 14, 2020, 9 pages.

International Search Report from PCT/EP2018/069151, dated Sep. 14, 2018, 5 pages.

International Search Report from PCT/EP2018/069157, dated Sep. 14, 2018, 5 pages.

International Search Report from PCT/EP2022/062018, dated Sep. 7, 2022, 5 pages.

International Search Report Issued in Counterpart Application No. PCT/EP2020/071660 Mailed Oct. 13, 2020.

Janeway, Jr., Charles A., et al. "Immunobiology" 5th Ed., Garland Science, pp. 117-118, 2001.

Jendeberg, Lena, et al. "Engineering of Fc1 and Fc3 from human immunoglobulin G to analyse subclass specificity for staphylococcal protein A1" Journal of Immunological Methods, vol. 201, pp. 25-34, Feb. 1997.

Jespers, Laurent S., et al. "Guiding the Selection of Human Antibodies from Phage Display Repertoires to a Single Epitope of an Antigen" Bio/Technology, vol. 12, No. 9, pp. 899-903, Sep. 1994. Abstract provided.

Jevsevar, Simona, et al. "PEGylation of therapeutic proteins" Biotechnology Journal: Healthcare Nutrition Technology, vol. 5, No. 1, pp. 113-128, Jan. 2010.

Jones, Andrew J.S. "Analysis of polypeptides and proteins" Advanced Drug Delivery Reviews, vol. 10, pp. 29-90, Jan.-Apr. 1993.

Kageyama, et al., "Adoptive Transfer of MAGE-A4 T-cell Receptor Gene-Transduced Lymphocytes in Patients with Recurrent Esophageal Cancer," Clinical Cancer Research, (2015), vol. 21, No. 10: 2268-2277.

Kessler, Jan H., et al. "Efficient Identification of Novel HLA-A*0201-presented Cytotoxic T Lymphocyte Epitopes in the Widely Expressed Tumor Antigen PRAME by Proteasome-mediated Digestion Analysis" Journal Exp. Med., vol. 193, No. 1, pp. 73-88, Jan. 2001.

Kirin, Srecko I., et al. "Amino Acid and Peptide Bioconjugates of Copper(II) and Zinc(II) Complexes with a Modified N, N-Bis(2-picolyl)amine Ligand" Inorganic Chemistry, vol. 44, pp. 5405-5415, Jul. 2005. Abstract provided.

Knapp, Bernhard, et al. "Variable Regions of Antibodies and T Cell Receptors May Not Be Sufficient in Molecular Simulations Investigating Binding" Journal of Chemical Theory and Computation, vol. 13, pp. 3097-3105, Jun. 2017.

Knies, Diana, et al. "An optimized single chain TCR scaffold relying on the assembly with the native CD3-complex prevents residual mispairing with endogenous TCRs in human T-cells" Oncotarget, vol. 7, No. 16, pp. 21199-21221, Mar. 2016.

Koiko, R, et al., "Biology of T-Lymphocytes," Immunology: Textbook, Chapter 8, "Academia" Publishing Center, pp. 121-122 (2008) with English translation.

Kontermann, Roland E., et al. "Complement recruitment using bispecific diabodies" Nature Biotechnology, vol. 15, No. 7, pp. 629-631, Jul. 1997. Abstract provided.

Kontermann, Roland E., et al. "Enzyme immunoassays using bispecific diabodies" Immunothechnology, vol. 3, No. 2, pp. 137-144, Jun. 1997.

Kuwana, Yoshihisa, et al. "Expression of Chimeric Receptor Composed of Immunoglobulin-Derived V Resions and T-Cell Receptor-Derived C Regions", vol. 149, No. 3, pp. 960-968, Dec. 31, 1987.

(56) References Cited

OTHER PUBLICATIONS

Lacy, Susan E., et al. "Generation and characterization of ABT-981, adual variable domain immunoglobulin (DVD-IgTM)molecule that specifically and potentlyneutralizes both IL-1aand IL-1b" mAbs, vol. 7, pp. 605-619, May/Jun. 2015.

Lefranc, Marie-Paule, et al. "IMGT unique numbering for immunoglobulin and T cell receptor variable domains and Ig superfamily V-like domains" Developmental & Comparative Immunology, vol. 27, No. 1, pp. 55-77, 2003.

Lefranc, Marie-Paule, et al. "IMGTR, the international ImMunoGeneTics information system(R) 25 years on" Nucleic Acids Research, vol. 43, Database issue D413-D422, Jan. 2015.

Lefranc, Marie-Paule, IMGT, the international ImMunoGeneTics database, » Nucleic Acids Research, vol. 29, No. 1, pp. 207-209 (2001).

Li, Hongmin, et al. "Structure-function studies of T-cell receptor-superantigen interactions" Immunological Reviews, vol. 163, No. 1, pp. 177-186, Jun. 1998 (abstract provided).

Linette, Gerald P. et al., "Cardiovascular toxicity and titin cross-reactivity of affinity-enhanced T cells in myeloma and melanoma", Blood, Aug. 8, 2013, pp. 863-871, vol. 122, No. 6.

Liu, Liqin, et al. "MGD011, a CD19 x CD3 Dual-Affinity Retargeting Bi-specific Molecule Incorporating Extended Circulating Half-life for the Treatment of B-Cell Malignancies" Clinical Cancer Research, vol. 23, No. 6, pp. 1506-1518, Mar. 2017.

Manning et al., "Alanine Scanning Mutagenesis of an αβ T Cell Receptor: Mapping the Energy of Antigen Recognition," Immunity, (1998), vol. 8: 413-425.

Mason, John O., et al. "Transcription Cell Type Specificity Is Conferred by an Immunoglobulin VH Gene Promoter That Includes a Functional Consensus Sequence" Cell, vol. 41, pp. 479-487, Jun. 1985.

Merchant, A.M., et al. "An efficient route to human bispecific IgG" Nature Biotechnology, vol. 16, No. 7, pp. 677-681, Jul. 1998.

Merten, Christoph, et al. "Directed Evolution of Retrovirus Envelope Protein Cytoplasmic Tails Guided by Functional Incorporation into Lentivirus Particles" Jounral of Virology, vol. 79, No. 2, pp. 834-840, Jan. 2005.

Miles, John J., et al. "Understanding the complexity and malleability of T-cell recognition" Immunology and Cell Biology, vol. 93, No. 5, pp. 433-441, May 2015.

Mitchell, Rod T., et al. "Intratubular germ cell neoplasia of the human testis: heterogeneous protein expression and relation to invasive potential" Modern Pathology, vol. 27, pp. 255-266, Sep. 2014.

Miyaji, Hiromasa, et al. "Expression of human beta-interferon in Namalwa KJM-1 which was adapted to serum-free medium" Cytotechnology, vol. 3, No. 2, pp. 133-140, Mar. 1990. Abstract provided.

Mizukami, Yuji, et al. "Primary T-Cell Lymphoma of the Thyroid" Pathology International, vol. 37, Issue 12, pp. 1987-1995, Dec. 1987. Abstract provided.

Moore, Paul A., et al. "Application of dual affinity retargeting molecules to achieve optimal redirected T-cell killing of B-cell lymphoma" Blood, vol. 117, No. 17, pp. 4542-4551, Apr. 2011.

Morgan, A., et al. "The N-terminal end of the CH2 domain of chimeric human IgG1 anti-HLA-DR is necessary for C1q, FcγRI and FcγRIII binding", Immunology, vol. 86, pp. 319-324, Oct. 1995.

Morgan, Richard A., et al. "Cancer Regression in Patients After Transfer of Genetically Engineered Lymphocytes" Science, vol. 314, pp. 126-129, Oct. 6, 2006.

Morrison, Sherie L., et al. "Chimeric human antibody molecules: Mouse antigen-binding domains with human constant region domains" Proc. Natl. Acad. Sci., vol. 81, pp. 6851-6855, Nov. 1984.

Nakatsugawa et al., "Identification of an HLA-A*0201-restricted cytotoxic T lymphocyte epitope from the lung carcinoma antigen, Lengsin," International Journal of Oncology, (2011), vol. 39: 1041-1049.

Needleman, Saul B., et al. "A general Method Applicable to the Search for Similarities in the Amino Acid Sequence of Two Proteins" Journal Molecular Biology, vol. 48, pp. 443-453, Mar. 1970. Abstract provided.

Neuberger, M.S., et al. "A hapten-specific chimaeric IgE antibody with human physiological effector function" Nature, vol. 314, pp. 268-270, Mar. 1985. Abstract provided.

O'Hare, K., et al. "Transformation of mouse fibroblasts to methotrexate resistance by a recombinant plasmid expressing a prokaryotic dihydrofolate reductase" Proceedings of the National Academy of Sciences, vol. 78, No. 3, pp. 1527-1531, Mar. 1981.

Ohkuri et al., "Identification of novel helper epitopes of MAGE-A4 tumor antigen: useful tool for the propagation of ThI cells" British Journal of Cancer (2009) pp. 1135-1143.

Onuoha, Shimobi C., et al. "Rational Design of Antirheumatic Prodrugs Specific for Sites of Inflammation" Arthritis & Rheumatology, vol. 67, No. 10, pp. 2661-2672, Oct. 2015.

O'Shea, Erin K., et al. "Peptide 'Velcro*': design of a heterodimeric coiled coil" Current Biology, vol. 3, No. 10, pp. 658-667, Oct. 1993.

Paul et al., "Fundamental Immunology: Third Edition," Raven Press, pp. 292-295, 1993.

Piccione, Emily C., "A bispecific antibody targeting CD47 and CD20 selectively binds and eliminates dual antigen expressing lymphoma cells" mAbs, vol. 7, No. 5, pp. 946-956, Sep. 2015.

Piepenbrink et al., "The basis for limited specificity and MHC restriction in a T cell receptor interface," Nature Communications, (2013), vol. 4: 1948.

Plebanski, Magdalena, et al. "Induction of peptide-specific primary cytotoxic T lymphocyte responses from human peripheral blood" European Journal of Immunology, vol. 25, No. 6, pp. 1783-1787, Jun. 1995.

Popovic et al., "The only proposed T-cell epitope derived from the TEL-AML 1 translocation is not naturally processed," Blood, (2011), vol. 118, No. 4: 946-954.

Portolano et al., "Lack of Promiscuity in Autoantigen-Specific H and L Chain Combinations as Revealed by Human H and L Chain 'Roulette'," J Immunol., (1993), vol. 150, No. 3: 880-7.

Rader, Christoph. "CARTs take aim at BiTEs" Blood, vol. 117, No. 17, pp. 4403-4404, Apr. 28, 2011.

Reichmann, Lutz, et al. "Reshaping human antibodies for therapy" Nature, vol. 332, No. 24, pp. 323-327, Mar. 1988.

Reiter, Yoram, et al. "Stabilization of the Fv Fragments in Recombinant Immunotoxins by Disulfide Bonds Engineered into Conserved Framework Regions" Biochemistry, vol. 33, pp. 5451-5459, May 1994.

Rice, Peter, et al. "EMBOSS: The European Molecular Biology Open Software Suite" Trend in Genetics, vol. 16, No. 6, pp. 276-277, Jun. 2000.

Richman, Sarah A., et al. "Structural features of T cell receptor variable regions that enhance domain stability and enable expression as single-chain V-alpha V-beta fragments" Molecular Immunology, vol. 46, pp. 902-916, 2009 (with 4 pp. of Supplementary Fig. 1 attached).

Roomp, Kirsten, et al. "Predicting interactions between T cell receptors and MHC-peptide complexes" Molecular Immunology, vol. 48, No. 4, pp. 553-562, Jan. 2011.

Rosenberg, Steven A., et al. "Use of Tumor-Infiltrating Lymphocytes and Interleukin-2 in the Immunotherapy of Patients with Metastatic Melanoma" New England Journal of Medicine, vol. 319, pp. 1676-1680, Dec. 1988. [Abstract Only].

Rudikoff et al., "Single amino acid substitution altering antigen-binding specificity," Proc. Natl. Acad. Sci. USA, vol. 79. pp. 1979-1983, Mar. 1982.

Sarcevic, Bozena, et al. "Expression of Cancer/Testis Tumor Associated Antigens in Cervical Squamous Cell Carcinoma" Oncology, vol. 64, No. 4, pp. 443-449, 2003.

Scaviner, Dominique, et al. "The Human T Cell Receptor Alpha Variable (TRAV) Genes" Experimental and Clinical Immunogenetics, vol. 17, No. 1, pp. 83-96, 2000.

Schellenberger, V., et al. "A recombinant polypeptide extends the in vivo half-life of peptides and proteins in a tunable manner" Nature Biotechnology, vol. 27, No. 12, pp. 1186-1190, Dec. 2009.

(56) References Cited

OTHER PUBLICATIONS

Schlapschy, Martin, et al. "PASylation: a biological alternative to PEGylation for extending the plasma half-life of pharmaceutically active proteins" Protein Eng Des Sel. vol. 26, No. 8, pp. 489-501, Aug. 2013.

Shao, Hongwei, et al. "TCR mispairing in genetically modified T cells was detected by fluorescence resonance energy transfer" Molecular Biology Reports, vol. 37, pp. 3951-3956, Apr. 2010.

Shearman, Clyde W., et al. "Construction, expression and characterization of humanized antibodies directed against the human alpha/beta T cell receptor" Journal of Immunology, vol. 147, No. 12, pp. 4366-4373, Dec. 15, 1991.

Shirakura, et al., "T-cell receptor gene therapy targeting melanoma-associated antigen-A4 inhibits human tumor growth in non-obese diabetic/SCID/ycnull mice," Cancer Science, (2012), vol. 103, No. 1: 17-25.

Shitara, Kenya, et al. "A new vector for the high level expression of chimeric antibodies in myeloma cells" Journal of Immunological Methods, vol. 167, No. 1-2, pp. 271-278, Jan. 1994.

Shopes, Bob. "A genetically engineered human IgG mutant with enhanced cytolytic activity" The Journal of Immunology, vol. 148, No. 9, pp. 2918-2922, May 1992.

Smith, Sheena N., et al. "T Cell Receptor Engineering and Analysis Using the Yeast Display Platform" Methods Mol Biology vol. 1319, pp. 95-141, 2015.

Sommermeyer, Daniel, et al. "Minimal Amino Acid Exchange in Human TCR Constant Regions Fosters Improved Function of TCR Gene-Modified T Cells" The Journal of Immunology, vol. 184, pp. 6223-6231, May 2010.

Spel, Lotte, et al. "Natural killer cells facilitate PRAME-specific T-cell reactivity against neuroblastoma" Oncotarget, vol. 6, No. 34, pp. 35770-35781, Oct. 2015.

Sun et al., "T cell receptor alpha chain V-J-region, partial [*Homo sapiens*]," GenBank: BAS03461.1, Jul. 22, 2015.

Sun et al., "T cell receptor alpha chain V-J-region, partial [*Homo sapiens*]," GenBank: BAS03441.1, Jul. 22, 2015.

Sun et al., "T cell receptor beta chain V-D-J-region, partial [*Homo sapiens*]," GenBank: BAS03679.1, Jul. 22, 2015.

Sun et al., "T cell receptor beta chain V-D-J-region, partial [*Homo sapiens*]," GenBank: BAS03896.1, Jul. 22, 2015.

Tao, Mi-Hua, et al. "Studies of Aglycosylated Chimeric Mouse-Human IgG: Role of carbohydrate in the structure and effector functions mediated by the human IgG constant region" The Journal of Immunology, vol. 143, No. 8, pp. 2595-2601, Oct. 1989.

Thotakura, Nageswara, et al. "Enzymatic Deglycosylation of Glycoproteins" Methods in Enzymology, vol. 138, pp. 350-359, Jan. 1987.

Urlaub, Gail, et al. "Isolation of Chinese hamster cell mutants deficient in dihydrofolate reductase acitivity" Proc. Natl. Acad. Sci., vol. 77, No. 7, pp. 4216-4220, Jul. 1980.

Wang, Bao-Zhong, et al. "Incorporation of High Levels of Chimeric Human Immunodeficiency Virus Envelope Glycoproteins into Virus-Like Particles" Journal of Virology, vol. 81, No. 20, pp. 10869-10878, Oct. 2007.

Wei, Hudie, et al. "Structural basis of a novel heterodimeric Fc for bispecific antibody production" Oncotarget, vol. 8, No. 31, pp. 51037-51049, Aug. 2017.

Winkler, Karsten, et al. "Changing the Antigen Binding Specificity by Single Point Mutations of an Anti-p24 (HIV-1) Antibody" Journal of Immunology, vol. 165, No. 8, pp. 4505-4514, Oct. 2000.

Wong, Wing Ki, et al. "Comparative Analysis of the CDR Loops of Antigen Receptors" Frontiers in Immunology, vol. 10, Article 2454, Oct. 2019.

Written Opinion from PCT/EP2022/062018, dated Sep. 7, 2022, 6 pages.

Wu, Chengbin, et al. "Molecular construction and optimization of anti-human IL-1α/β dual variable domain immunoglobulin (DVD-Ig™) molecules" mAbs, vol. 1, No. 4, pp. 339-347, Jul. 2009.

Wu, Chengbin, et al. "Simultaneous targeting of multiple disease mediators by a dual-variable-domain immunoglobulin" Nature Biotechnology, vol. 25, No. 11, pp. 1290-1297, Nov. 2007.

Yang et al., "Structural basis for clonal diversity of the human T-cell response to a dominant influenza virus epitope," J. Biol. Chem., vol. 292, No. 45; pp. 18618-18627 (2017).

Zhang, Tong, et al. "Transgenic TCR expression: comparison of single chain with full-length receptor constructs for T-cell function" Cancer Gene Therapy, vol. 11, pp. 487-496, May 2004.

Zheng-Cai, Jia et al. "Identification of Two Novel HLA-A*0201-Restricted CTL Epitopes Derived from MAGE-A4", Clinical and Developmental Immunology, 2010, Article ID 567594.

Zhu, Zhenping, et al. "Identifcation of Heavy Chain Residues in a Humanized Anti-CD3 Antibody Important for Efficient Antigen Binding and T Cell Activation" Journal of Immunology, vol. 155, No. 4, pp. 1903-1910, Aug. 15, 1995.

\* cited by examiner

PEPTIDES AND COMBINATION OF PEPTIDES FOR USE IN IMMUNOTHERAPY AGAINST NON-SMALL CELL LUNG CANCER AND OTHER CANCERS

CROSS REFERENCE TO RELATED APPLICATIONS

This application is a divisional of U.S. patent application Ser. No. 16/681,472, filed on Nov. 12, 2019, which is a continuation of U.S. patent application Ser. No. 15/460,396, filed on Mar. 16, 2017, which claims benefit of U.S. Provisional Application No. 62/308,944, filed Mar. 16, 2016, and Great Britain Application No. 1604458.8, filed Mar. 16, 2016. The entire contents of each of these applications is herein incorporated by reference for all purposes.

This application also is related to PCT/EP2017/056049 filed 15 Mar. 2017, the content of which is incorporated herein by reference in its entirety.

REFERENCE TO SEQUENCE LISTING SUBMITTED AS A COMPLIANT XML FILE (.xml)

Pursuant to the EFS-Web legal framework and 37 CFR §§ 1.821-825 (see MPEP § 2442.03(a)), a Sequence Listing in the form of a compliant xml file (entitled "2912919-061003_Sequence-Listing_ST26" created on Dec. 7, 2023, and 23,676 bytes in size) is submitted concurrently with the instant application, and the entire contents of the Sequence Listing are incorporated herein by reference.

FIELD

The present description relates to peptides, proteins, nucleic acids and cells for use in immunotherapeutic methods. In particular, the present description relates to the immunotherapy of cancer. The present description furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

The present description further relates to the use of the above peptides for the generation of specific T-cell receptors (TCRs) binding to tumor-associated antigens (TAAs) for targeting cancer cells, the generation of T-cells expressing same, and methods for treating cancers using same. The novel peptide sequences and their variants derived from HLA class I molecules of human tumor cells can be used in vaccine compositions for eliciting anti-tumor immune responses, or as targets for the development of pharmaceutically/immunologically active compounds and cells. Preferred is a peptide that has the amino acid sequence KVLEHVVRV (SEQ ID NO: 1).

BACKGROUND OF THE INVENTION

Non-small cell lung cancer (NSCLC) is named according to the size of the cancer cells when observed under a microscope and has to be differentiated from small cell lung cancer (SCLC). NSCLC accounts to about 85% to 90% of all lung cancers (American Cancer Society, 2015).

Both lung cancers (SCLC and NSCLC) are the second most common cancer in both men and women. Lung cancer is leading cause of cancer death, which accounts for about 25%. Thus, more people die of lung cancer than of colon, breast, and prostate cancers combined each year. Furthermore, both lung cancers account for about 13% (more than 1.8 million) of all new cancers. Lung cancer mainly occurs in older people. The average age at the time of diagnosis is about 70. Fewer than 2% of all cases are diagnosed in people younger than 45.

There are four major types of NSCLC, namely, adenocarcinoma, squamous cell carcinoma, bronchoalveolar carcinoma, and large cell carcinoma. Adenocarcinoma and squamous cell carcinoma are the most common types of NSCLC based on cellular morphology (Travis et al., Lung Cancer Principles and Practice, Lippincott-Raven, New York, 361-395, 1996). Adenocarcinomas are characterized by a more peripheral location in the lung and often have a mutation in the K-ras oncogene (Gazdar et al., Anticancer Res., 14, 261-267, 1994). Squamous cell carcinomas are typically more centrally located and frequently carry p53 gene mutations (Niklinska et al., Folia Histochem. Cytobiol., 39, 147-148, 2001).

Many genetic alterations associated with development and progression of lung cancer have been reported, but the precise molecular mechanisms remain unclear (Sozzi, G. Eur. J. Cancer 37: 63-73 (2001)). The majority of NSCLCs are characterized by the presence of the ras mutation thereby rendering the patient relatively insensitive to treatment by known kinase inhibitors. As a result, current treatments of lung cancer are generally limited to cytotoxic drugs, surgery, and radiation therapy. Over the last decade newly developed cytotoxic agents including paclitaxel, docetaxel, gemcitabine, and vinorelbine have emerged to offer multiple therapeutic choices for patients with advanced NSCLC; however, each of the new regimens can provide only modest survival benefits compared with cisplatin-based therapies (Schiller, J. H. et al., N. Engl. J. Med. 346: 92-98 (2002); Kelly, K. et al., J. Clin. Oncol. 19: 3210-3218 (2001)). Hence, new therapeutic strategies, such as development of molecular-targeted agents, are eagerly awaited by clinicians.

Immunotherapy of cancer represents an option of specific targeting of cancer cells while minimizing side effects. Cancer immunotherapy makes use of the existence of tumor associated antigens.

The current classification of tumor associated antigens (TAAs) can be categorized into the following groups:

Cancer-testis antigens: The first TAAs ever identified that can be recognized by T-cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T-cells in normal tissues and can therefore be considered as immunologically tumor-specific. Well-known examples for CT antigens are the MAGE family members and NY-ESO-1.

Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

Tumor-specific antigens: These unique TAAs arise from mutations of normal genes (such as 0-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides. MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g., during endocytosis, and are subsequently processed.

Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. It is well known that the TCR, the peptide and the MHC are thereby present in a stoichiometric amount of 1:1:1.

CD4-positive helper T-cells play an important role in inducing and sustaining effective responses by CD8-positive cytotoxic T-cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T-cell (CTL-) friendly cytokine milieu (Mortara et al., 2006) and attract effector cells, e.g., CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006). Elongated (longer) peptides of the description can function as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate antitumor immune responses.

It was shown in mammalian animal models, e.g., mice, that even in the absence of CD8-positive T lymphocytes, CD4-positive T-cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T-cells as direct antitumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T-cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T-cells bearing specific T-cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e., copy numbers of the respective peptide per cell). Tumor-specific and tumor-associated antigens are often derived from proteins directly involved in transformation of a normal cell to a tumor cell due to their function, e.g., in cell cycle control or suppression of apoptosis. Additionally, downstream targets of the proteins directly causative for a transformation may be up-regulated und thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, and leads to an in vitro or in vivo T-cell-response.

Therefore, TAAs are a starting point for the development of a T-cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T-cell with a corresponding TCR has to be present and the immunological tolerance for this particular epitope needs to be absent or minimal. In a very preferred embodiment of the description it is therefore important to select only those over- or selectively presented peptides against which a functional and/or a proliferating T-cell can be found. Such a functional T-cell is defined as a T-cell, which upon stimulation with a specific antigen can be clonally expanded and is able to execute effector functions ("effector T-cell").

In case of targeting peptide-MHC by specific TCRs (e.g., soluble TCRs) and antibodies or other binding molecules (scaffolds) according to the description, the immunogenicity of the underlying peptides is secondary. In these cases, the presentation is the determining factor.

In spite of significant progress in basic and clinical research concerning TAAs (Rosenbeg et al., Nature Med. 4: 321-7 (1998); Mukherji et al., Proc. Natl. Acad. Sci. USA 92: 8078-82 (1995); Hu et al., Cancer Res. 56: 2479-83 (1996)), only limited number of candidate TAAs for the treatment of cancer are available. TAAs abundantly expressed in cancer cells, and at the same time which expression is restricted to cancer cells would be promising candidates as immunotherapeutic targets. Further, identification of new TAAs inducing potent and specific antitumor immune responses is expected to encourage clinical use of peptide vaccination strategy in various types of cancer (Boon and can der Bruggen, J. Exp. Med. 183: 725-9 (1996); van der Bruggen et al., Science 254: 1643-7 (1991); Brichard et al., J. Exp. Med. 178: 489-95 (1993); Kawakami et al., J. Exp. Med. 180: 347-52 (1994); Shichijo et al., J. Exp. Med. 187: 277-88 (1998); Chen et al., Proc. Natl. Acad. Sci. USA 94: 1914-8 (1997); Harris, J. Natl. Cancer Inst. 88: 1442-5 (1996); Butterfield et al., Cancer Res. 59: 3134-42 (1999); Vissers et al., Cancer Res. 59: 5554-9 (1999); van der Burg et al., J Immunol 156: 3308-14 (1996); Tanaka et al., Cancer Res. 57: 4465-8 (1997); Fujie et al., Int. J. Cancer 80: 169-72 (1999); Kikuchi et al., Int. J. Cancer 81: 459-66 (1999); Oiso et al., Int. J. Cancer 81: 387-94 (1999)).

Furthermore, although advances have been made in the development of molecular-targeting drugs for cancer therapy, the ranges of tumor types that respond as well as the effectiveness of the treatments are still very limited. Hence, it is urgent to develop new anticancer agents that target molecules highly specific to malignant cells and are likely to cause minimal or no adverse reactions. There is also a need to identify factors representing biomarkers for cancer in general and NSCLC in particular, leading to better diagnosis of cancer, assessment of prognosis, and prediction of treatment success.

In an aspect, the present description relates to a peptide comprising an amino acid sequence selected from the group consisting of SEQ ID NO:1 to SEQ ID NO:24 or a variant sequence thereof which is at least 65%, preferably at least 77%, and more preferably at least 85% homologous (preferably at least 75% or at least 85% identical) to SEQ ID NO:1 to SEQ ID NO:24, wherein said variant binds to MHC and/or induces T-cells cross-reacting with said peptide, or a pharmaceutically acceptable salt thereof, and wherein said peptide is not the underlying full-length polypeptide.

The present description further relates to a peptide of the present description comprising a sequence that is selected from the group consisting of SEQ ID NO:1 to SEQ ID NO:24 or a variant thereof, which is at least 65%, preferably at least 75%, and more preferably at least 85% homologous (preferably at least 75% or at least 85% identical) to SEQ ID NO:1 to SEQ ID NO:24, wherein said peptide or variant thereof has an overall length of between 8 and 100, preferably between 8 and 30, and most preferably of between 8 and 14 amino acids, wherein said peptide or variant binds to MHC and/or induces T-cells cross-reacting with said peptide, or a pharmaceutically acceptable salt thereof.

The following tables show peptides according to the present description, and their respective SEQ ID Nos.

TABLE 1

Peptides according to the present description.

| SEQ ID NO: | Sequence |
|---|---|
| 1 | KVLEHVVRV |
| 2 | KVLEHVVRL |
| 3 | KVLEHVVRA |
| 4 | KVLEHVVRI |
| 5 | KLLEHVVRV |

TABLE 1-continued

Peptides according to the present description.

| SEQ ID NO: | Sequence |
|---|---|
| 6 | KLLEHVVRL |
| 7 | KLLEHVVRA |
| 8 | KLLEHVVRI |
| 9 | KALEHVVRV |
| 10 | KALEHVVRL |
| 11 | KALEHVVRA |
| 12 | KALEHVVRI |
| 13 | YLLEHVVRV |
| 14 | YLLEHVVRL |
| 15 | YLLEHVVRA |
| 16 | YLLEHVVRI |
| 17 | YALEHVVRV |
| 18 | YALEHVVRL |
| 19 | YALEHVVRA |
| 20 | YALEHVVRI |
| 21 | YVLEHVVRV |
| 22 | YVLEHVVRL |
| 23 | YVLEHVVRA |
| 24 | YVLEHVVRI |

In another aspect, the present description relates to a MAG-003 peptide, for example an isolated peptide, comprising an amino acid sequence according to the following general formula I:

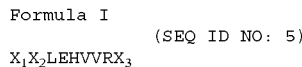

Formula I
(SEQ ID NO: 5)
$X_1X_2LEHVVRX_3$ wherein $X_1$ is selected from the amino acids K and Y, $X_2$ is selected from the amino acids V, L and A, and $X_3$ is selected from V, L, A, and I, wherein said peptide binds to an HLA class I or class II molecule and/or induces T-cells cross-reacting with said peptide, or a pharmaceutically acceptable salt thereof. In an aspect, said peptide is not the underlying full-length polypeptide.

The present description furthermore generally relates to the peptides according to the present description for use in the treatment of proliferative diseases, such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

Particularly preferred are the peptides—alone or in combination—according to the present description selected from the group consisting of SEQ ID NO:1 to SEQ ID NO:24. More preferred are the peptides—alone or in combination—selected from the group consisting of SEQ ID NO:1 to SEQ ID NO:24 (see Table 1), and their uses in the immunotherapy of non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably glioblastoma, gastric cancer, lung cancer, hepatocellular carcinoma, colorectal cancer, pancreatic cancer, esophageal cancer, ovarian cancer, and non-small cell lung cancer.

The present description furthermore relates to peptides according to the present description that have the ability to bind to a molecule of the human major histocompatibility complex (MHC) class-I or in an elongated form, such as a length-variant MHC class-II.

The present description further relates to the peptides according to the present description wherein said peptides (each) comprise, consist of, or consist essentially of an amino acid sequence according to SEQ ID NO:1 to SEQ ID NO:24.

The present description further relates to the peptides according to the present description, wherein said peptide is modified and/or includes non-peptide bonds.

The present description further relates to the peptides according to the present description, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present description further relates to a nucleic acid, encoding the peptides according to the present description. The present description further relates to the nucleic acid according to the present description that is DNA, cDNA, PNA, RNA or combinations thereof.

The present description further relates to an expression vector capable of expressing and/or expressing a nucleic acid according to the present description.

The present description further relates to a peptide according to the present description, a nucleic acid according to the present description or an expression vector according to the present description for use in the treatment of diseases and in medicine, in particular in the treatment of cancer.

The present description further relates to antibodies that are specific against the peptides according to the present description or complexes of said peptides according to the present description with MHC, and methods of making these.

The present description further relates to a host cell comprising a nucleic acid according to the present description or an expression vector as described before.

The present description further relates to the host cell according to the present description that is an antigen presenting cell, and preferably is a dendritic cell.

The present description further relates to a method for producing a peptide according to the present description, said method comprising culturing the host cell according to the present description, and isolating the peptide from said host cell or its culture medium.

The present description further relates to said method according to the present description, wherein the antigen is loaded onto class I or II MHC molecules expressed on the surface of a suitable antigen-presenting cell or artificial antigen-presenting cell by contacting a sufficient amount of the antigen with an antigen-presenting cell.

The present description further relates to the method according to the present description, wherein the antigen-presenting cell comprises an expression vector capable of expressing and/or expressing said peptide containing SEQ ID NO:1 to SEQ ID No.: 24, preferably containing SEQ ID NO:1 to SEQ ID NO:24, or a variant amino acid sequence.

The present description further relates to activated T-cells, produced by the method according to the present description, wherein said T-cell selectively recognizes a cell which expresses a polypeptide comprising an amino acid sequence according to the present description.

The present description further relates to a method of killing target-cells in a patient which target-cells aberrantly express a polypeptide comprising any amino acid sequence according to the present description, the method comprising administering to the patient an effective number of T-cells as produced according to the present description.

The present description further relates to the use of any peptide as described, the nucleic acid according to the present description, the expression vector according to the present description, the cell according to the present description, the activated T lymphocyte, the T-cell receptor or the antibody or other peptide- and/or peptide-MHC-binding molecules according to the present description as a medicament or in the manufacture of a medicament. Preferably, said medicament is active against cancer.

Preferably, said medicament is a cellular therapy, a vaccine or a protein based on a soluble TCR or antibody.

The present description further relates to a use according to the present description, wherein said cancer cells are non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably non-small cell lung cancer.

The present description further relates to biomarkers based on the peptides according to the present description, herein called "targets," that can be used in the diagnosis of cancer, preferably non-small cell lung cancer. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC. Optionally the antibody carries a further effector function such as an immune stimulating domain or toxin.

The present description further relates to the use of these novel targets for the identification of TCRs that recognize at least one of said targets, and preferably the identification of said TCRs that activate T-cells.

The present description also relates to the use of these novel targets in the context of cancer treatment.

The present description further relates to the use of the peptides according to the invention for the production of TCRs, individual TCR subunits (alone or in combination), and subdomains thereof, in particular soluble TCR (sTCRs) and cloned TCRs, said TCRs engineered into autologous or allogeneic T-cells, and methods of making same, as well as other cells bearing said TCR or cross-reacting with said TCRs.

The present description further relates to a TCR protein, individual TCR subunits (alone or in combination), and subdomains thereof, in particular soluble TCR (sTCRs) and cloned TCRs that bind to a KVLEHVVRV (SEQ ID NO:1)-HLA-A*02 complex comprising a TCR alpha chain variable domain and a TCR beta chain variable domain.

The present description further relates to an isolated nucleic acid comprising a nucleotide sequence encoding a TCR of the present description. The present description further relates to a recombinant expression vector comprising a nucleic acid encoding a TCR alpha chain, beta chain, or both, as produced according to the present description.

The present description further relates to an isolated host cell comprising the recombinant expression vector expressing the nucleic acid encoding the TCR alpha chain, beta chain, or both, of the present description.

The present description further relates to an isolated host cell comprising the recombinant expression vector of the present description, preferably wherein the cell is a peripheral blood lymphocyte (PBL).

The present description further relates to an isolated PBL comprising the recombinant expression vector of the present description, wherein the PBL is a CD8+ T-cell or a CD4+ T-cell.

The present description further relates to a population of cells comprising at least one host cell of the present description.

The present description further relates to TCR proteins of the present description for use in the treatment of proliferative diseases, such as, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T-cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (elongated variants of the peptides of the description) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present description differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids.

The length of the oligopeptide is not critical to the description, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the description as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present description), if it is capable of inducing an immune response. In the case of the present description, immunogenicity is more specifically defined as the ability to induce a T-cell response. Thus, an "immunogen" would be a molecule that is capable of inducing an immune response, and in the case of the present description, a molecule capable of inducing a T-cell response. In another aspect, the immunogen can be the peptide, the complex of the peptide with MHC, oligopeptide, and/or protein that is used to raise specific antibodies or TCRs against it.

A class I T-cell "epitope" requires a short peptide that is bound to a class I MHC receptor, forming a ternary complex (MHC class I alpha chain, beta-2-microglobulin, and peptide) that can be recognized by a T-cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 2

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The MAGEA4 gene is a member of the MAGLA gene family. The members of this family encode proteins with 50 to 80% sequence identity to each other. The promoters and first exons of the MAGLA genes show considerable variability, suggesting that the existence of this gene family enables the same function to be expressed under different transcriptional controls. The MAGLA genes are clustered at chromosomal location Xq28. They have been implicated in some hereditary disorders, such as dyskeratosis congenita. At least four variants encoding the same protein have been found for this gene. [provided by RefSeq, July 2008]

MAGEA4 localization has been described as cytoplasmic (Kim et al., 2015). However, MAGEA4 staining has also been detected in nuclei, with differential distribution between nucleus and cytoplasm in well-differentiated versus less differentiated cancers (Sarcevic et al., 2003).

MAGEA4 is used as a male germ cell marker. It is not expressed in gonocytes, but expressed in pre-spermatogonia and mature germ cells (Mitchell et al., 2014).

MAGEA4 is an oncofetal protein or cancer testis antigen. There is no clear evidence for a direct tumor-promoting effect of MAGEA4. One study suggests that overexpression of MAGEA4 promotes growth of spontaneously transformed normal oral keratinocytes by inhibiting cell cycle arrest and apoptosis (Bhan et al., 2012). However, other reports suggest a tumor-suppressive effect of MAGEA4 in vitro, since overexpression increased apoptosis and caspase-3 activity, while MAGEA4 silencing resulted in decreased caspase-3 activity (Peikert et al., 2006). Others reported that a C-terminal fragment of MAGEA4 has proapoptotic activity in vitro (Sakurai et al., 2004) and that it inhibits anchorage-independent growth through its interaction with the oncoprotein gankyrin (Nagao et al., 2003).

There is sporadic evidence for an association with tumor metastasis: MAGEA4 expression has been associated with lymph node metastasis in esophageal squamous cell carcinoma (Forghanifard et al., 2011), with progression to muscle-invasive cancer in bladder cancer (Bergeron et al., 2009), and with lymph node metastases in vulvar cancer (Bellati et al., 2007).

There is no clear evidence for association of MAGEA4 with cancer stem-like cells. However, MAGEA4 expression has been detected in side population cells from different cancer cell lines, including lung, colon, and breast (Yamada et al., 2013), as well as in Hodgkin lymphoma tumor samples (Shafer et al., 2010). Moreover, MAGEA4 has been described in undifferentiated human embryonic stem cells as well as their differentiated derivatives, teratocarcinoma cells (Lifantseva et al., 2011).

Over-expression of MAGEA4 in cancer—MAGEA4 expression has been described in a multitude of different cancer types. For details on specific cancer entities, see subsections below. Listed here is only some further information on cancer types not covered by a specific section below.

In primary melanoma, expression of MAGEA4 has been detected by immunohistochemistry in 10-30% of tumors and up to 44% in distant metastases (Barrow et al., 2006; Luftl et al., 2004). Primary mucosal melanomas of the head and neck showed up to 60% positivity for MAGEA4 staining (Prasad et al., 2004).

In bladder cancer, MAGEA4 was observed in 38% of nonmuscle-invasive tumors, 48% of muscle-invasive tumors, 65% of carcinomas in situ and in 73% of lymph node metastases (Bergeron et al., 2009). Another study described MAGEA4 expression in bladder cancer with somewhat lower frequencies, with highest frequencies in squamous ($25/55$, 46%) as compared to adeno ($4/15$, 27%), sarcomatoid ($4/14$, 29%), small cell ($5/20$, 25%) or transitional cell (281/1,522, 19%) carcinomas (Kocher et al., 2002). In urothelial carcinoma, MAGEA4 expression was detected by immunohistochemistry in 64% and by RT-PCR in 58% of cases (Sharma et al., 2006). MAGEA4 was detected by RT-PCR in 40-60% of head and neck squamous cell carcinoma samples (Cuffel et al., 2011; Soga et al., 2013).

MAGEA4 expression was detected in 57% of oral squamous cell carcinoma samples (Montoro et al., 2012; Ries et al., 2005). MAGEA4 expression was not detected by immunohistochemistry in any of 70 benign and malignant thyroid tumor samples analyzed (Melo et al., 2011). MAGEA4 expression was only found in classic seminoma but not in nonseminomatous testicular germ cell tumors (Aubry et al., 2001; Bode et al., 2014). MAGEA4 expression was detected in 14% ($5/35$) of gastrointestinal stomal tumors (Perez et al., 2008).

In childhood medulloblastoma, MAGEA4 mRNA was detected in 28% ($7/25$), but immunoreactivity was only observed in 4% ($1/25$) of samples (Oba-Shinjo et al., 2008). Another study found weak MAGEA4 mRNA in 18% ($2/11$) of medulloblastomas (Jacobs et al., 2008).

One study found MAGEA4 to be expressed in 60% of adult T-cell leukemia/lymphoma samples (Nishikawa et al., 2012). Another report described much lower expression frequencies in 5% ($2/38$) of non-Hodgkin lymphoma samples, and 20-30% of Hodgkin disease samples. In Hodgkin lymphoma, Reed-Sternberg cells were the most strongly stained cells whereas the surrounding cells were not (Chambost et al., 2000). MAGEA4 expression was not detected in 39 multiple myeloma samples (Andrade et al., 2008).

MAGEA4 immunoreactivity was detectable in 33% of cervical squamous cell carcinomas ($20/60$) (Sarcevic et al., 2003).

MAGEA4 expression was found to be present in 12% of endometrioid adenocarcinomas, 63% of uterine papillary serous carcinomas and 91% of uterine carcinosarcomas by immunohistochemistry. Within the tumor population, the extent of MAGEA4 expression was highest in the carcinosarcomas (Resnick et al., 2002).

MAGEA4 staining as detected by immunohistochemistry is heterogeneous, and only a fraction of positive tumors expresses MAGEA4 in more than 50% of the tumors cells (Resnick et al., 2002; Sarcevic et al., 2003).

In contrast to the large number of studies reporting MAGEA4 expression in different cancer types, evidence for association of MAGEA4 with outcome and prognosis is more limited. However, some reports find a correlation of MAGEA4 expression with clinical parameters. In head and neck squamous cell carcinoma, MAGEA4 expression has been correlated with poor overall survival and was an independent prognostic indicator of poor outcome (Cuffel et al., 2011). In bladder cancer, MAGEA4 expression was correlated with recurrence and progression to muscle-invasive cancer (Bergeron et al., 2009), and strong MAGEA4 staining has been associated with decreased survival (Kocher et al., 2002). In gastrointestinal stromal tumors, expression of MAGEA4 together with other cancer testis antigens was correlated with recurrence (Perez et al., 2008), and also in vulvar cancer, MAGEA4 was more frequently detected in recurrent tumors (Bellati et al., 2007).

Evidence for association of MAGEA4 expression with advanced tumor stages is provided by some reports covering different cancer types: In malignant melanoma, MAGEA4 expression increased with advancing disease from 9% in primary tumors to 44% in distant metastases (Barrow et al., 2006). Also in vulvar cancer, MAGEA4 expression was more frequent in tumors with lymph node metastases (Bellati et al., 2007). Moreover, MAGEA4 expression was associated with high-grade tumors or advanced stage in endometrial carcinoma (Chitale et al., 2005), cervical squamous cell carcinomas (Sarcevic et al., 2003), and bladder cancer (Bergeron et al., 2009; Kocher et al., 2002).

MAGEA4 appears to be expressed by tumor cells, there is no evidence for expression in stromal, vascular, immune or other tumor-associated cells. Moreover, MAGEA4 expression has also been detected in cultured tumor cell lines, such as gastric cancer cell lines (Li et al., 1997), esophageal carcinoma cell lines (Tanaka et al., 1997), pancreatic carcinoma cell lines (Kubuschok et al., 2004) and head and neck squamous cell carcinoma cell lines (Hartmann et al., 2015).

TABLE 3

MAGEA4 as general cancer target

| Antigen properties | Evaluation |
|---|---|
| Over-expression in [cancer of interest] reported in literature | |
| Over-expression in other cancers reported in literature | + |
| T-cell responses against source protein-derived targets described | + |
| Oncofetal expression pattern | + |
| Expression by cancer stem cells | (−) |
| Roles in cell cycle progression and tumor cell proliferation | (−) |
| Involvement in tumor invasion, migration and metastasis | |
| Link to cancer-associated signaling pathways[1] | |
| Anti-apoptotic effects | (−) |
| Pro-angiogenic effects/Neovascularisation | |
| Over-expression linked to poor prognosis in cancer | + |
| Over-expression associated with advanced cancer stages | + |
| General cancer target | |
| Sub-cellular localization[2] | CY |
| Characterization of source protein in literature (−, +, ++, +++) | + |
| Cell type association[3] | TU |

[1]TGF = Transforming growth factor; PI3K = Phosphatidylinositide 3-kinases; p53 = cellular tumor antigen p53; EGFR = epithelial growth factor receptor; FGF2 = fibroblast growth factor 2; Wnt = Wnt/beta-catenin pathway (embryogenesis); Ras = Rat sarcoma proto-oncogene; NF–kB = Nuclear factor Kappa B (eukaryotic transcription factor)
[2]CY = cyto-plasmic;
[3]TU = tumor cells MAGEA4 as therapeutic target Immunotherapy target (vaccines, adjuvants, CARs) Twenty patients with advanced esophageal, stomach or lung cancer were administered MAGEA4 vaccine containing 300 g protein subcutaneously once every 2 weeks in six doses. Of 15 patients who completed one vaccination cycle, four patients showed a MAGEA4-specific humoral response, and these patients showed longer overall survival than patients without antibody response. CD4 and CD8T-cell responses were observed in three and six patients, respectively, and patients with induction of MAGEA4-specific IFNγ-producing CD8T-cells, but not CD4T-cells, lived longer than those without induction (Saito et al., 2014).

There is a case report on a colon cancer patient with pulmonary metastases who was treated with the fusion peptide MAGE-A4-H/K-HELP (consisting of MAGE-A4 (278-299) helper epitope fused to MAGE-A4(143-154) killer epitope by a glycine linker) together with OK432 and Montanide. The treatment induced MAGEA4-specific Th1 and CTL immune responses and MAGEA4-specific IgG. Tumor growth and carcinoembryonic antigen tumor marker were decreased in the final diagnosis (Takahashi et al., 2012).

A phase I clinical trial investigated adoptive transfer of TCR-engineered autologous CTLs reactive towards MAGEA4 (143-151) bound to HLA-A*24:02 in esophageal cancer patients. Patients were given TCR-transduced lymphocytes once, without preconditioning treatment, followed by subcutaneous immunizations with MAGEA4 peptide after 2 and 4 weeks. No objective tumor regression was observed, possibly due to the lack of lymphodepleting regimen and administration of IL2 (Kageyama et al., 2015). Preclinical studies in mice had demonstrated that transferred T-cells inhibited growth of MAGEA4-expressing tumor cell lines inoculated in the mice, and that additional peptide vaccination enhanced this antitumor activity (Shirakura et al., 2012).

Targeting MAGEA4 with adoptive CTL transfer is proposed as a treatment option of EBV-negative Hodgkin and non-Hodgkin lymphoma. Infused CTLs targeting EBV-derived peptides have been described to induce complete remissions in EBV(+) lymphoma patients. Therefore, targeting other antigens expressed by lymphoma, including MAGEA4, is being explored as a possible treatment option (Cruz et al., 2011; Gerdemann et al., 2011).

Several studies have demonstrated the generation of MAGEA4 specific CD4(+) T-cells from healthy donors and cancer patients after incubation with autologous antigen-presenting cells pulsed with overlapping peptide pools (Cesson et al., 2011; Gerdemann et al., 2011; Ohkuri et al., 2009).

MAG-003, i.e., KVLEHVVRV (SEQ ID NO:1), is a HLA-A*0201-restricted cytotoxic T lymphocyte (CTL) epitope of MAGEA4 (amino acids 286-294). (Jia et al. 2010; Wu et al. 2011), the contents of which are hereby incorporated by reference in their entirety. In an aspect, MAG-003 elicits peptide-specific CTLs both in vitro from HLA-A*0201-positive PBMCs and in HLA-A*0201/Kb transgenic mice. In another aspect, the induced CTLs lyse target cells in an HLA-A*0201-restricted fashion, demonstrating that MAG-003 is HLA-A*0201-restricted CTL epitope and serve as a target for therapeutic antitumoral vaccination (Jia et al. 2010), the content of which is hereby incorporated by reference in its entirety.

In addition, the SYFPEITHI routine (Rammensee et al., 1997; Rammensee et al., 1999) predicts MAG-003 binding to A*02:01 with an absolute score of 25 and a relative score of 0.69. The present inventors confirmed 100% of identifications are from MAG-003 binding to A*02-positive samples.

TABLE 4

MAG-003 presentation in normal tissues and cancers.

| A*02 | Samples | Mean intensity | jScore |
|---|---|---|---|
| Normal | 0 of 245 | — | — |
| Cancer | 14 of 397 | 1.1e+07 | 0.000 |
| HCC | 1 of 16 | 2.9e+06 | 0.000 |
| MEL | 0 of 3 | 0.0e+00 | |
| OC | 2 of 20 | 4.0e+07 | 0.000 |
| pNSCLC | 11 of 91 | 1.0e+07 | 0.000 |

Over-presentation or specific presentation of TAAs on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

Surgically removed tissue specimens were provided as indicated above after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Gene expression analysis of tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, CA, USA), which includes RNA fragmentation, cDNA conversion and addition of sequencing adaptors. Libraries derived from multiple samples are mixed equimolarly and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Tables 5 to 7 show RNASeq data (expression scores) of MAG-003 expression in various cancers.

TABLE 5

RNASeq Score 1

| Tumor type | tgScore | exonScore (27242) | exonScore (317034) | exonScore (593984) |
|---|---|---|---|---|
| BRCA | 1.57 | 1.23 | 1.23 | 1.51 |
| CRC | 1.65 | 1.00 | 1.00 | 1.76 |
| HCC | 12.10 | 11.98 | 11.97 | 6.15 |
| OC | 56.60 | 18.45 | 18.44 | 57.74 |
| OSCAR | 58.42 | 3.49 | 3.49 | 60.40 |
| PC | 12.10 | 10.78 | 10.77 | 4.74 |
| pGB | 0.88 | 0.95 | 0.95 | 0.74 |
| pNSCLC | 100.83 | 1.52 | 1.52 | 98.57 |
| RCC | 0.93 | 0.95 | 0.95 | 0.77 |
| SCLC | 56.41 | 28.32 | 28.30 | 152.27 |

TABLE 6

RNASeq Score 3

| Tumor type | tgScore | exonScore (27242) | exonScore (317034) | exonScore (593984) |
|---|---|---|---|---|
| BRCA | 7.48 | 5.11 | 5.11 | 6.01 |
| CRC | 8.35 | 1.05 | 1.05 | 7.90 |
| HCC | 123.03 | 210.33 | 210.30 | 42.22 |
| OC | 612.59 | 333.74 | 333.69 | 447.29 |
| OSCAR | 632.95 | 47.41 | 47.40 | 468.45 |
| PC | 122.95 | 187.07 | 187.05 | 31.15 |
| pGB | 0.31 | 0.18 | 0.18 | 0.25 |
| pNSCLC | 1100.05 | 10.26 | 10.25 | 768.23 |
| RCC | 0.78 | 0.18 | 0.18 | 0.43 |
| SCLC | 611.00 | 524.23 | 524.17 | 1190.36 |

TABLE 7

Tumor expression

| Tumor type | tgtumor40 | Exontumor40 (27242) | Exontumor40 (317034) | Exontumor40 (593984) |
|---|---|---|---|---|
| BRCA | 0.12 | 0.04 | 0.04 | 0.17 |
| CRC | 0.14 | 0.01 | 0.01 | 0.22 |
| HCC | 2.05 | 1.82 | 1.82 | 1.18 |
| OC | 11.19 | 3.16 | 3.16 | 13.72 |

TABLE 7-continued

Tumor expression

| Tumor type | tgtumor40 | Exontumor40 (27242) | Exontumor40 (317034) | Exontumor40 (593984) |
|---|---|---|---|---|
| OSCAR | 10.89 | 0.42 | 0.42 | 13.11 |
| PC | 2.09 | 1.65 | 1.65 | 0.89 |
| pGB | 0.00 | 0.00 | 0.00 | 0.01 |
| pNSCLC | 19.25 | 0.09 | 0.09 | 22.58 |
| RCC | 0.01 | 0.00 | 0.00 | 0.01 |
| SCLC | 10.18 | 4.53 | 4.53 | 33.35 |

In contrast to the large number of studies reporting MAGEA4 expression in different cancer types, evidence for association of MAGEA4 with outcome and prognosis is more limited. However, some reports find a correlation of MAGEA4 expression with clinical parameters. In head and neck squamous cell carcinoma, MAGEA4 expression has been correlated with poor overall survival and was an independent prognostic indicator of poor outcome (Cuffel et al., 2011). An inverse correlation was found between MAGE-A4 expression and patient survival in advanced stage NSCLC cancers (Yoshida et al., 2006; Shigematsu et al., 2010) and ovarian cancers (Yakirevich et al., 2003). In bladder cancer, MAGEA4 expression was correlated with recurrence and progression to muscle-invasive cancer (Bergeron et al., 2009), and strong MAGEA4 staining has been associated with decreased survival (Kocher et al., 2002). In gastrointestinal stomal tumors, expression of MAGEA4 together with other cancer testis antigens was correlated with recurrence (Perez et al., 2008), and also in vulvar cancer, MAGEA4 was more frequently detected in recurrent tumors (Bellati et al., 2007).

In the Cancer Genome Atlas (TCGA) study of high-grade serous ovarian cancers, below median MAGEA8 expression was associated with 11.4 months increased PFS making, it was the strongest verifiable effect. High expression of MAGE A8 was associated with poorer PFS in patients with high CD3 tumors, potentially indicating an immunosuppressive role of MAGEA8 such as via activation of immunosuppressive Tregs (Eng et al., 2015).

High-risk group and low-risk group of colon cancer patients were distinguished by eight biomarkers (ZBTB32, OR51B4, CCL8, TMEFF2, SALL3, GPSM1, MAGEA8, and SALL1) which provided reference for individual treatment (Zhang et al., 2015).

In human squamous cell carcinomas cell line experiments MAGE-A5 and –A8 were reported as negative predictors of anti-EGFR therapy using panitumumab (Hartmann et al., 2014).

Evidence for association of MAGEA4 expression with advanced tumor stages is provided by some reports covering different cancer types: In malignant melanoma, MAGEA4 expression increased with advancing disease from 9% in primary tumors to 44% in distant metastases (Barrow et al., 2006). Also in vulvar cancer, MAGEA4 expression was more frequent in tumors with lymph node metastases (Bellati et al., 2007). Moreover, MAGEA4 expression was associated with high-grade tumors or advanced stage in endometrial carcinoma (Chitale et al., 2005), cervical squamous cell carcinomas (Sarcevic et al., 2003), and bladder cancer (Bergeron et al., 2009; Kocher et al., 2002).

In an embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this description are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein the term "a nucleotide coding for (or encoding) a TCR protein" refers to a nucleotide sequence coding for the TCR protein including artificial (man-made) start and stop codons compatible for the biological system the sequence is to be expressed by, for example, T-cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. In an aspect, such polynucleotides are part of a vector and/or such polynucleotides or polypeptides are part of a composition, and still are isolated in that such vector or composition is not part of its natural environment.

The polynucleotides, and recombinant or immunogenic polypeptides, disclosed in accordance with the present description may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present description, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present description can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present description, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=100[1−(C/R)]

wherein C is the number of differences between the Reference Sequence and the Compared Sequence over the length of alignment between the Reference Sequence and the Compared Sequence, wherein
  each base or amino acid in the Reference Sequence that does not have a corresponding aligned base or amino acid in the Compared Sequence and
  each gap in the Reference Sequence and
  each aligned base or amino acid in the Reference Sequence that is different from an aligned base or amino acid in the Compared Sequence, constitutes a difference and
  the alignment has to start at position 1 of the aligned sequences; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

s mentioned above, the present description thus provides a peptide comprising a sequence that is selected from the group of consisting of SEQ ID NO:1 to SEQ ID NO:24 or a variant thereof which is 85% homologous to SEQ ID NO:1 to SEQ ID NO:24, or a variant thereof that will induce T-cells cross-reacting with said peptide. The peptides of the description have the ability to bind to a molecule of the human major histocompatibility complex (MHC) class-I or elongated versions of said peptides to class II.

In the present description, the term "homologous" refers to the degree of identity (see percent identity above) between sequences of two amino acid sequences, i.e., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T-cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence consisting of SEQ ID NO:1 to SEQ ID NO:24. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T-cells. Similarly, a TCR protein may be modified so that it at least maintains, if not improves, the ability to interact with and bind to a suitable MHC molecule/ KVLEHVVRV (SEQ ID NO:1) complex, such as HLA-A*02 or -DR, and in that way it at least maintains, if not improves, the ability to activate T-cells.

These T-cells can subsequently cross-react with cells and kill cells that express a polypeptide that contains the natural amino acid sequence of the cognate peptide, such as KVLEHVVRV (SEQ ID NO:1), as defined in the aspects of the description. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO:1 to SEQ ID NO 24, by maintaining the known anchor residues, and would be able to determine whether such variants maintain the ability to bind MHC class I or II molecules/ KVLEHVVRV (SEQ ID NO:1) complexes. The variants of the present description retain the ability to bind MHC class I or II molecules/KVLEHVVRV (SEQ ID NO:1) complexes. T-cells expressing the variants of the present description can subsequently kill cells that express a polypeptide containing the natural amino acid sequence of the cognate peptide, such as KVLEHVVRV (SEQ ID NO:1).

The original (unmodified) peptides or TCR proteins as disclosed herein can be modified by the substitution of one or more residues at different, possibly selective, sites within the peptide chain, if not otherwise stated. Preferably those substitutions are located at the end of the amino acid chain of said peptide. For TCR proteins, preferably those substitutions are located at variable domains of TCR alpha chain and TCR beta chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the description and yet still be encompassed by the disclosure herein. In addition, non-standard amino acids (i.e., other than the common naturally occurring proteinogenic amino acids) may also be used for substitution purposes to produce immunogens and immunogenic polypeptides according to the present description.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the TCR can be modified by replacement with other amino acids whose incorporation do not substantially affect T-cell reactivity and does not eliminate binding to the relevant MHC. Thus, apart from the proviso given, the peptide of the description may be any peptide (by which term the inventors include oligopeptide or polypeptide), which includes the amino acid sequences or a portion or variant thereof as given.

TABLE 8

Variants of the peptides of the invention
Position

| 1 | 2 | 3 | 4 | 5 | 6 | 7 | 8 | 9 |
|---|---|---|---|---|---|---|---|---|
| | | | | SEQ ID NOs: 1-13 | | | | |
| K | V | L | E | H | V | V | R | V |
| | | | | Variants | | | | |
| Y | L | | | | | | | |
| Y | L | | | | | | | L |
| Y | L | | | | | | | A |
| Y | L | | | | | | | I |
| Y | A | | | | | | | |
| Y | A | | | | | | | L |
| Y | A | | | | | | | A |
| Y | A | | | | | | | I |
| Y | | | | | | | | |
| Y | | | | | | | | L |
| Y | | | | | | | | A |
| Y | | | | | | | | I |

Longer (elongated) peptides may also be suitable. It is possible that MHC class I epitopes, although usually the actual epitope are residues that do not substantially affect proteolytic cleavage necessary to expose the actual epitope during processing.

The peptides of the description can be elongated by up to four amino acids, that is 1, 2, 3 or 4 amino acids can be added to either end in any combination between 8 and 11 amino acids long, are generated by peptide processing from longer peptides or proteins that include the actual epitope. It is preferred that the residues that flank between 4:0 and 0:4. Combinations of the elongations according to the description can be found in Table 9.

TABLE 9

Combinations of the elongations of peptides of the description

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present description may be identical to naturally occurring tumor-associated or tumor-specific epitopes or may include epitopes that differ by no more than four residues from the reference peptide, as long as they have substantially identical anti-genic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present description provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present description will have the ability to bind to a molecule of the human major histocompatibility complex (MHC) class I or II. Binding of a peptide or a variant to a MHC complex may be tested by methods known in the art.

Preferably, when the T-cells specific for a peptide according to the present description are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T-cells from more than one individual, at least two, and more preferably three individuals.

Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens (Aleksic et al. 2012; Kunert et al. 2013). It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance (Xing et al. 2012; Ruella et al. 2014; Sharpe et al. 2015), meaning that only T-cells with low-affinity TCRs for self antigens remain. Therefore, affinity of TCRs or variants of the present description to MAG-003 have been enhanced by methods well known in the art as described below.

A "pharmaceutical composition" is a composition suitable for administration to a human being in a medical setting. Preferably, a pharmaceutical composition is sterile and produced according to GMP guidelines.

The pharmaceutical compositions comprise the peptides or TCR proteins either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, ptoluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like. Another embodiment of the present invention relates to a non-naturally occurring peptide wherein said peptide consists or consists essentially of an amino acid sequence according to SEQ ID No: 1 to SEQ ID No: 24 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions $PO_4^{3-}$, $SO_4^{2-}$, $CH_3COO^-$, $Cl^-$, $Br^-$, $NO_3^-$, $ClO_4^-$, $I^-$, $SCN^-$ and as cations $NH_4^+$, $Rb^+$, $K^+$, $Na^+$, $Cs^+$, $Li^+$, $Zn^+$, $Mg^+$, $Ca^+$, $Mn^+$, $Cu^+$ and $Ba^+$. Particularly salts are selected from $(NH_4)_3PO_4$, $(NH_4)_2HPO_4$, $(NH_4)H_2PO_4$, $(NH_4)_2SO_4$, $NH_4CH_3COO$, $NH_4Cl$, $NH_4Br$, $NH_4NO_3$, $NH_4ClO_4$, $NH_4I$, $NH_4SCN$, $Rb_3PO_4$, $Rb_2HPO_4$, $RbH_2PO_4$, $Rb_2SO_4$, $Rb_4CH_3COO$, $Rb_4Cl$, $Rb_4Br$, $Rb_4NO_3$, $Rb_4ClO_4$, $Rb_4I$, $Rb_4SCN$, $K_3PO_4$, $K_2HPO_4$, $KH_2PO_4$, $K_2SO_4$, $KCH_3COO$, $KCl$, $KBr$, $KNO_3$, $KClO_4$, $KI$, $KSCN$, $Na_3PO_4$, $Na_2HPO_4$, $NaH_2PO_4$, $Na_2SO_4$, $NaCH_3COO$, $NaCl$, $NaBr$, $NaNO_3$, $NaClO_4$, $NaI$, $NaSCN$, $ZnCl_2$ $Cs_3PO_4$, $Cs_2HPO_4$, $CsH_2PO_4$, $Cs_2SO_4$, $CsCH_3COO$, $CsCl$, $CsBr$, $CsNO_3$, $CsClO_4$, $CsI$, $CsSCN$, $Li_3PO_4$, $Li_2HPO_4$, $LiH_2PO_4$, $Li_2SO_4$, $LiCH_3COO$, $LiCl$, $LiBr$, $LiNO_3$, $LiClO_4$, $LiI$, $LiSCN$, $Cu_2SO_4$, $Mg_3(PO_4)_2$, $Mg_2HPO_4$, $Mg(H_2PO_4)_2$, $Mg_2SO_4$, $Mg(CH_3COO)_2$, $MgCl_2$, $MgBr_2$, $Mg(NO_3)_2$, $Mg(ClO_4)_2$, $MgI_2$, $Mg(SCN)_2$, $MnCl_2$, $Ca_3(PO_4)$, $Ca_2HPO_4$, $Ca(H_2PO_4)_2$, $CaSO_4$, $Ca(CH_3COO)_2$, $CaCl_2$, $CaBr_2$, $Ca(NO_3)_2$, $Ca(ClO_4)_2$, $CaI_2$, $Ca(SCN)_2$, $Ba_3(PO_4)_2$, $Ba_2HPO_4$, $Ba(H_2PO_4)_2$, $BaSO_4$, $Ba(CH_3COO)_2$, $BaCl_2$, $BaBr_2$, $Ba(NO_3)_2$, $Ba(ClO_4)_2$, $BaI_2$, and $Ba(SCN)_2$. Particularly preferred are NH acetate, $MgCl_2$, $KH_2PO_4$, $Na_2SO_4$, KCl, NaCl, and $CaCl_2$, such as, for example, the chloride or acetate (trifluoroacetate) salts.

In an especially preferred embodiment, the pharmaceutical compositions comprise the peptides or TCR proteins as salts of acetic acid (acetates), trifluoro acetates or hydrochloric acid (chlorides).

A further aspect of the description provides a nucleic acid (for example a polynucleotide) encoding a peptide or peptide variant and a TCR protein and TCR variants of the description. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the description provides an expression vector capable of expressing a polypeptide according to the description.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, CN, USA.

A desirable method of modifying the DNA encoding the polypeptide of the description employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, poxor adenovirus vectors are preferred.

The DNA (or in the case of retroviral vectors, RNA) may then be expressed in a suitable host to produce a polypeptide comprising the peptide or variant of the description. Thus, the DNA encoding the peptide or variant of the description may be used in accordance with known techniques, appropriately modified in view of the teachings contained herein, to construct an expression vector, which is then used to transform an appropriate host cell for the expression and production of the polypeptide of the description. Such techniques include those disclosed, for example, in U.S. Pat. Nos. 4,440,859, 4,530,901, 4,582,800, 4,677,063, 4,678, 751, 4,704,362, 4,710,463, 4,757,006, 4,766,075, and 4,810, 648.

The DNA (or in the case of retroviral vectors, RNA) encoding the polypeptide constituting the compound of the description may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the description are then cultured for a sufficient time and under appropriate conditions known to those skilled in the art in view of the teachings disclosed herein to permit the expression of the polypeptide, which can then be recovered.

Many expression systems are known, including bacteria (for example E. coli and Bacillus subtilis), yeasts (for example Saccharomyces cerevisiae), filamentous fungi (for example Aspergillus spec.), planT-cells, animal cells and insecT-cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, NJ, USA. An example of an inducible mammalian expression vector is pMSG, also available from Pharmacia. Useful yeast plasmid vectors are pRS403-406 and pRS413-416 and are generally available from Stratagene Cloning Systems, La Jolla, CA 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent-cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the description are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present description also relates to a host cell transformed with a polynucleotide vector construct of the present description. The host cell can be either prokaryotic or eukaryotic. Bacterial cells may be preferred prokaryotic host cells in some circumstances and typically are a strain of E. coli such as, for example, the E. coli strains DH5 available from Bethesda Research Laboratories Inc., Bethesda, MD, USA, and RR1 available from the American Type Culture Collection (ATCC) of Rockville, MD, USA (No ATCC 31343).

Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, CA 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect-cells are Sf9 cells which can be transfected with baculovirus expression vectors. An overview regarding the choice of suitable host cells for expression can be found in, for example, the textbook of Paulina Balbis and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present description is accomplished by well-known methods that typically depend on the type of vector used. With regard to transformation of prokaryotic host cells, see, for example, Cohen et al. (Cohen et al., 1972) and (Green and Sambrook, 2012). Transformation of yeast-cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, MD 20877, USA. Electroporation is also useful for transforming and/or transfecting cells and is well known in the art for transforming yeasT-cell, bacterial cells, insecT-cells and vertebrate cells.

Successfully transformed cells, i.e., cells that contain a DNA construct of the present description, can be identified by well-known techniques such as PCR. Alternatively, the presence of the protein in the supernatant can be detected using antibodies.

It will be appreciated that certain host cells of the description are useful in the preparation of the peptides of the description, for example bacterial, yeast and insecT-cells. However, other host cells may be useful in certain therapeutic methods. For example, antigen-presenting cells, such as dendritic cells, may usefully be used to express the peptides of the description such that they may be loaded into appropriate MHC molecules. Thus, the current description provides a host cell comprising a nucleic acid or an expression vector according to the description.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the description provides a method of producing a peptide or its variant, the method comprising culturing a host cell and isolating the peptide from the host cell or its culture medium.

In another embodiment the TCR proteins, the nucleic acid or the expression vector of the description are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g., between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g., Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T-cells for the respective opposite CDR as noted above.

The medicament of the description may also include one or more adjuvants. Adjuvants are substances that non-specifically enhance or potentiate the immune response (e.g., immune responses mediated by CD8-positive T-cells and helper-T (TH) cells to an antigen, and would thus be considered useful in the medicament of the present description. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, saponin-based adjuvant (e.g., ISCOMATRIX®), ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, Denileukin diftitox (ONTAK®), OspA, PepTel® vector system, poly (lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present description.

Other TLR binding molecules such as RNA binding TLR 7, TLR 8 and/or TLR 9 may also be used.

Other examples for useful adjuvants include, but are not limited to chemically modified CpGs (e.g., CpR, IDERA®), dsRNA analogues such as Poly(I:C) and derivates thereof (e.g., rintatolimod (AmpliGen®), poly-(ICLC) (Hiltonol®), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g., anti-CD40, anti-TGFbeta, anti-TNFalpha receptor) and SC58175, which may act therapeutically and/or as an adjuvant. The amounts and concentrations of adjuvants and additives useful in the context of the present description can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the description the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the description the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the description, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the description attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g., antigenic) determinant. In one embodiment, a scaffold is able to direct the entity to which it is attached (e.g., a (second) antigen binding moiety) to a target site, for example to a specific type of tumor cell or tumor stroma bearing the antigenic determinant (e.g., the complex of a peptide with MHC, according to the application at hand). In another embodiment a scaffold is able to activate signaling through its target antigen, for example a T-cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T-cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e., not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labeling which provides that the bound scaffold can be detected by determining the presence or absence of a signal provided by the label. For example, the scaffold can be labeled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present description further relates to aptamers. Aptamers (see for example WO 2014/191359 and the literature as cited therein) are short single-stranded nucleic acid molecules, which can fold into defined three-dimensional structures and recognize specific target structures.

They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. In an aspect, at least one or more aptamers are taken up by tumor cells and thus can function as molecular vehicles for the targeted delivery of anti-cancer agents such as siRNA into tumor cells.

Aptamers can be selected against complex targets such as cells and tissues and complexes of the peptides according to the description at hand with the MHC molecule, using the cell-SELEX (Systematic Evolution of Ligands by Exponential enrichment) technique.

The peptides of the present description can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the description to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the description to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present description are all explicitly incorporated by reference in their entireties.

Preferably, the antibody is binding with a binding affinity of below 20 nanomolar, preferably of below 10 nanomolar, to the complex, which is also regarded as "specific" in the context of the present description.

The present description relates to a TCR protein or a variant or functional fragment thereof that specifically binds to MAG-003.

The present description further relates to the TCR protein according to the description, wherein the TCR protein is (chemically) modified and/or includes non-peptide bonds.

The present description further relates to a nucleic acid, encoding the TCR proteins according to the description, provided that the TCR protein is not the complete (full) human protein.

The present description further relates to the nucleic acid according to the description that is DNA, cDNA, PNA, RNA or combinations thereof.

The present description further relates to an expression vector capable of expressing a nucleic acid according to the present description.

The present description further relates to a TCR protein according to the present description, a nucleic acid according to the present description or an expression vector according to the present description for use in medicine, in particular in the treatment of non-small cell lung cancer.

The present description further relates to a host cell comprising a nucleic acid according to the description or an expression vector according to the description.

The present description further relates to the host cell according to the present description that is a T-cell, and preferably a CD8-positive T-cell or CD4-positive T-cell.

The present description further relates to a method of producing a TCR protein according to the present description, said method comprising incubating PBMCs from HLA-A*02-negative healthy donors with A2/MAG-003 monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising incubating PBMCs from HLA-A*02-negative healthy donors with A2/p286-1Y2L monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising incubating PBMCs from HLA-A*02-negative healthy donors with A2/p286-1Y2L9L monomers, incubating the PBMCs with tetramer-phycoerythrin (PE) and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with MAG-003, incubating PBMCs obtained from the transgenic mice with tetramer-phycoerythrin (PE), and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L, incubating PBMCs obtained from the transgenic mice with tetramer-phycoerythrin (PE), and isolating the high avidity T-cells by fluorescence activated cell sorting (FACS)-Calibur analysis.

The present description further relates to a method of producing a TCR protein according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L9L, incubating PBMCs obtained from the transgenic mice with tetramer-phycoerythrin (PE), and isolating the high avidity T-cells by fluorescence activated cell sorting (FACS)-Calibur analysis.

The present description further relates to a method of killing target cells in a patient which target cells aberrantly express MAG-003, the method comprising administering to the patient an effective number of T-cells as according to the present description.

The present description further relates to the use of any TCR protein described, a nucleic acid according to the present description, an expression vector according to the present description, a cell according to the present description, or an activated cytotoxic T lymphocyte according to the present description as a medicament or in the manufacture of a medicament. The present description further relates to a use according to the present description, wherein the medicament is active against cancer.

The present description further relates to a use according to the description, wherein said cancer cells are non-small cell lung cancer cells or other solid or hematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The present description further relates to particular marker proteins and biomarkers based on the peptides according to the present description, herein called "targets" that can be used in the diagnosis and/or prognosis of non-small cell lung cancer. The present description also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g., CDRs, Fv, Fab and Fc fragments) or polymers of those immunoglobulin molecules and humanized versions of immunoglobulin molecules, as long as they exhibit any of the desired properties (e.g., specific binding of a non-small cell lung cancer marker (poly)peptide, delivery of a toxin to a non-small cell lung cancer cell expressing a cancer marker gene at an increased level, and/or inhibiting the activity of a non-small cell lung cancer marker polypeptide) according to the description.

Whenever possible, the antibodies of the description may be purchased from commercial sources. The antibodies of the description may also be generated using well-known methods. The skilled artisan will understand that either full length non-small cell lung cancer marker polypeptides or fragments thereof may be used to generate the antibodies of the description. A polypeptide to be used for generating an antibody of the description may be partially or fully purified from a natural source, or may be produced using recombinant DNA techniques.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the description may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the description can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')₂ fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment. The antibodies of the description may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the description are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating non-small cell lung cancer, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the description to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g., by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. In another aspect, it is expressed in T-cells used for adoptive transfer. See, for example, WO 2004/033685A1, WO 2004/074322A1, and WO 2013/057586A1, the contents of which are incorporated by reference in their entirety.

In addition, the peptides and/or the TCRs or antibodies or other binding molecules of the present description can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography.

Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

The present invention will be further described in the following examples, nevertheless, without being limited thereto. For the purposes of the present invention, all references as cited herein are incorporated by reference in their entireties.

EXAMPLES

Figure 1:
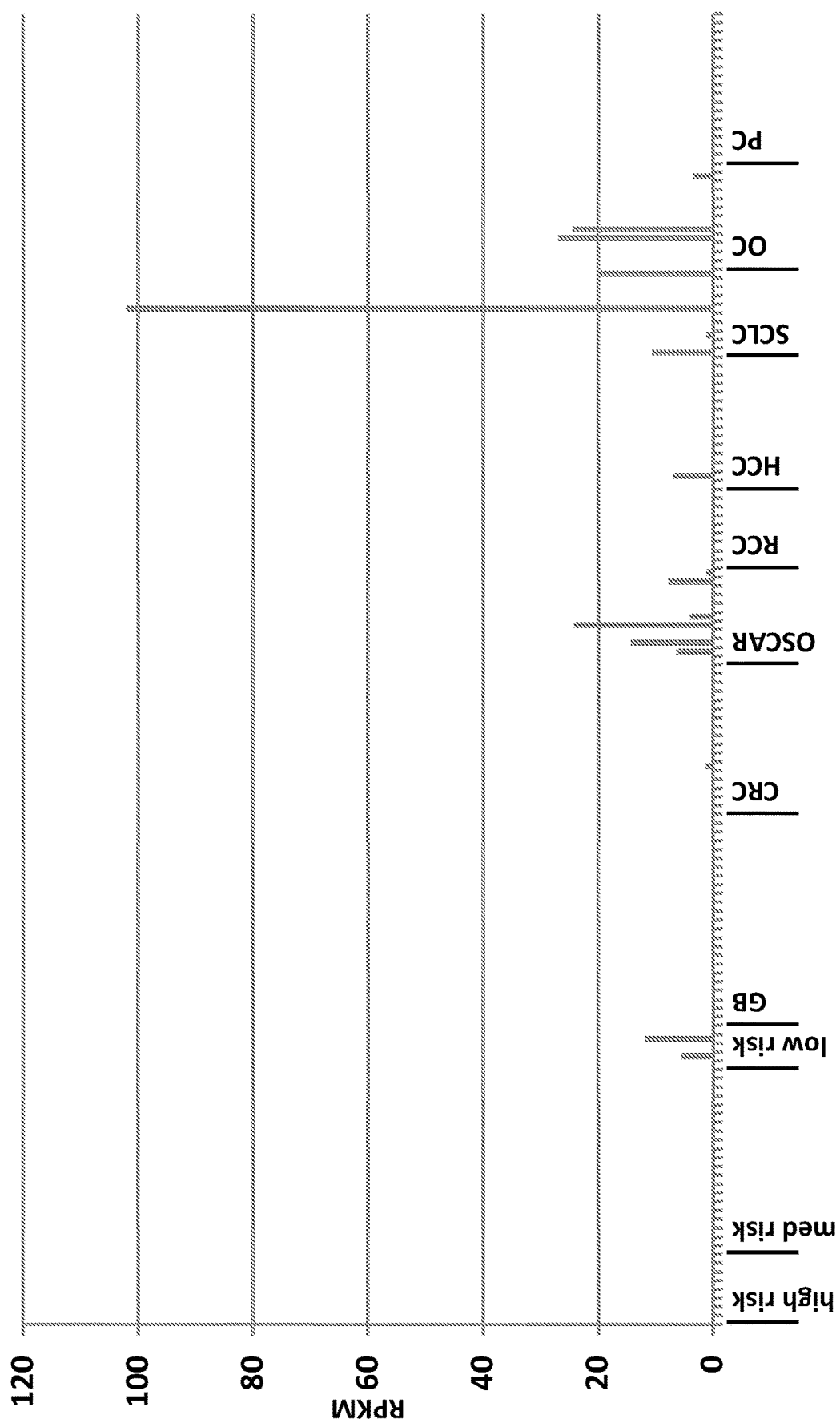
FIG. 1 shows MAG-003 exon expression in MAGEA4 (tumor versus healthy, RNASeq data). MAGE-003 exon expression in MAGEA4 on healthy tissues was compared to that on various solid tumors (red bars). Healthy tissue subtypes are grouped as high (dark green bars), medium (light green bars) and low risk tissues (grey bars). Each bar represents a single sample. High expression on normal tissues was only found in placenta and testis (low risk). (RPKM=reads per kilobase per million mapped reads)
Figure 2:
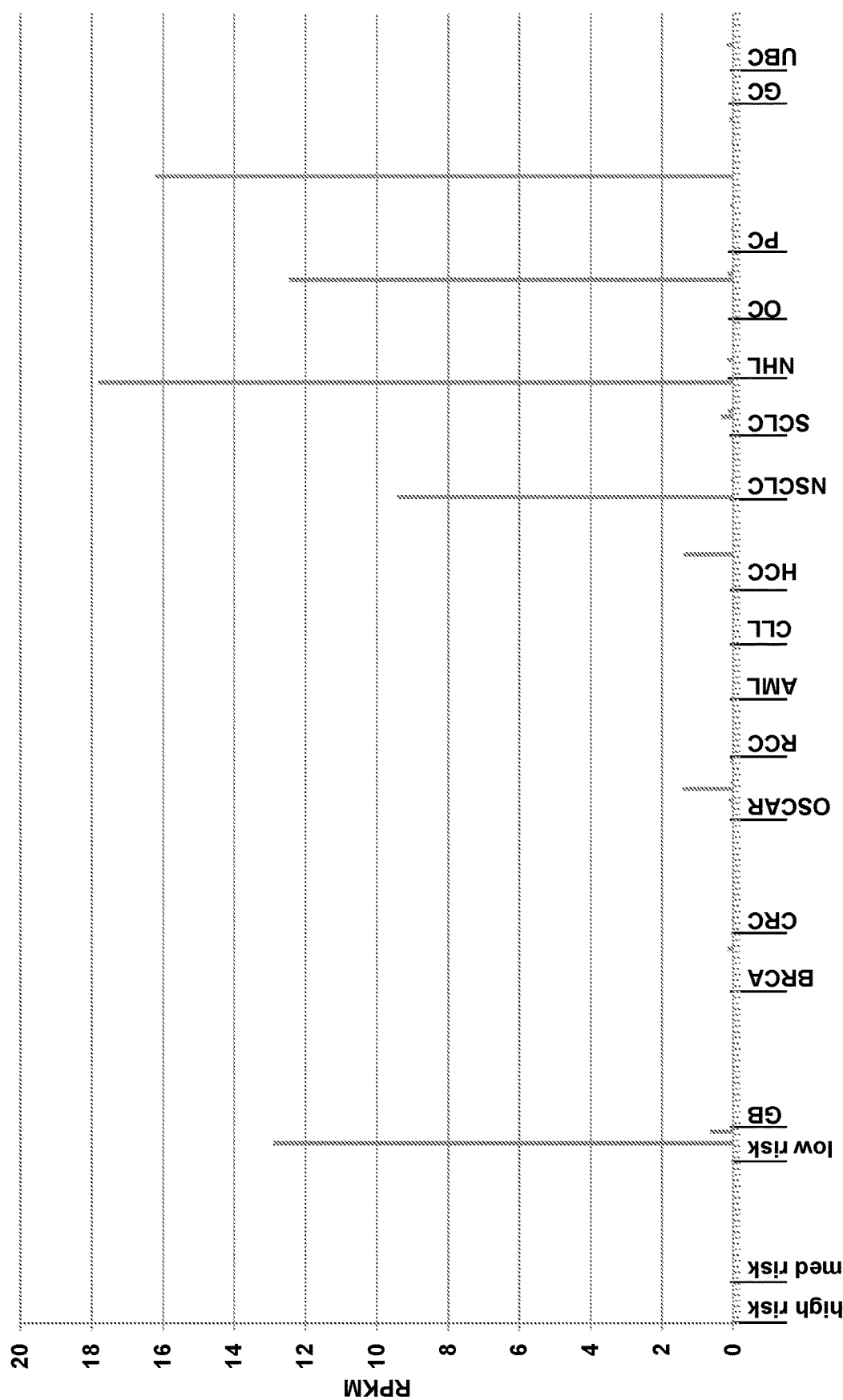
FIG. 2 shows MAG-003 exon expression on MAGEA8 (tumor versus healthy, RNASeq data). MAGEA8 exon expression on healthy tissues was compared to that on various solid tumors (red bars). Healthy tissue subtypes are grouped as high (dark green bars), medium (light green bars) and low risk tissues (grey bars). Each bar represents a single sample. High expression on normal tissues was only found in placenta (low risk). (RPKM=reads per kilobase per million mapped reads).
Figure 3:
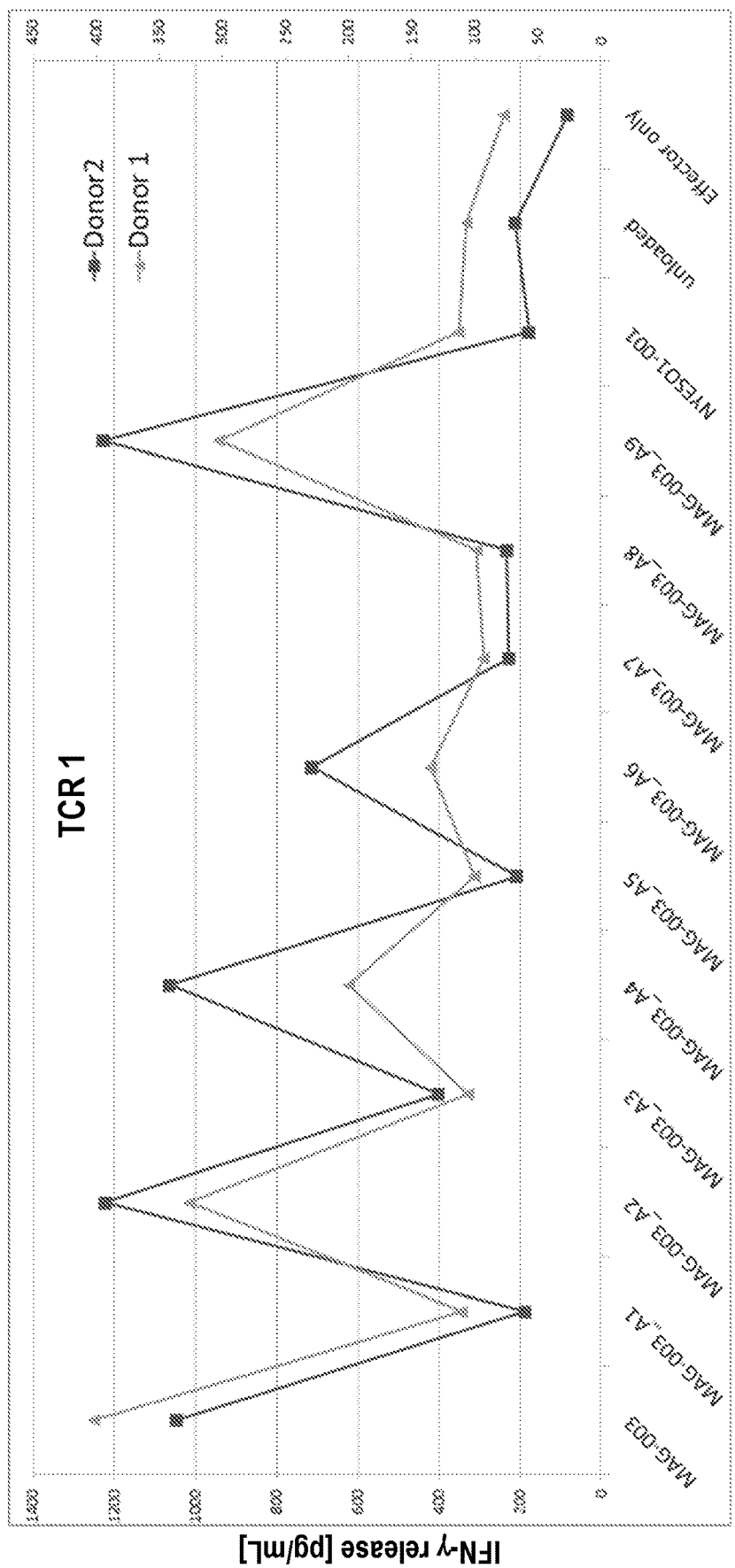
FIG. 3 shows IFNγ release from CD8+ T-cells electroporated with alpha and beta chain RNA of MAG-003 specific TCRs after co-incubation with target cells loaded with MAG-003 peptide (SEQ ID NO:1) or various MAG-003 alanine-substitution variants at positions 1-9 of SEQ ID NO:1 as disclosed herein.
Figure 4:
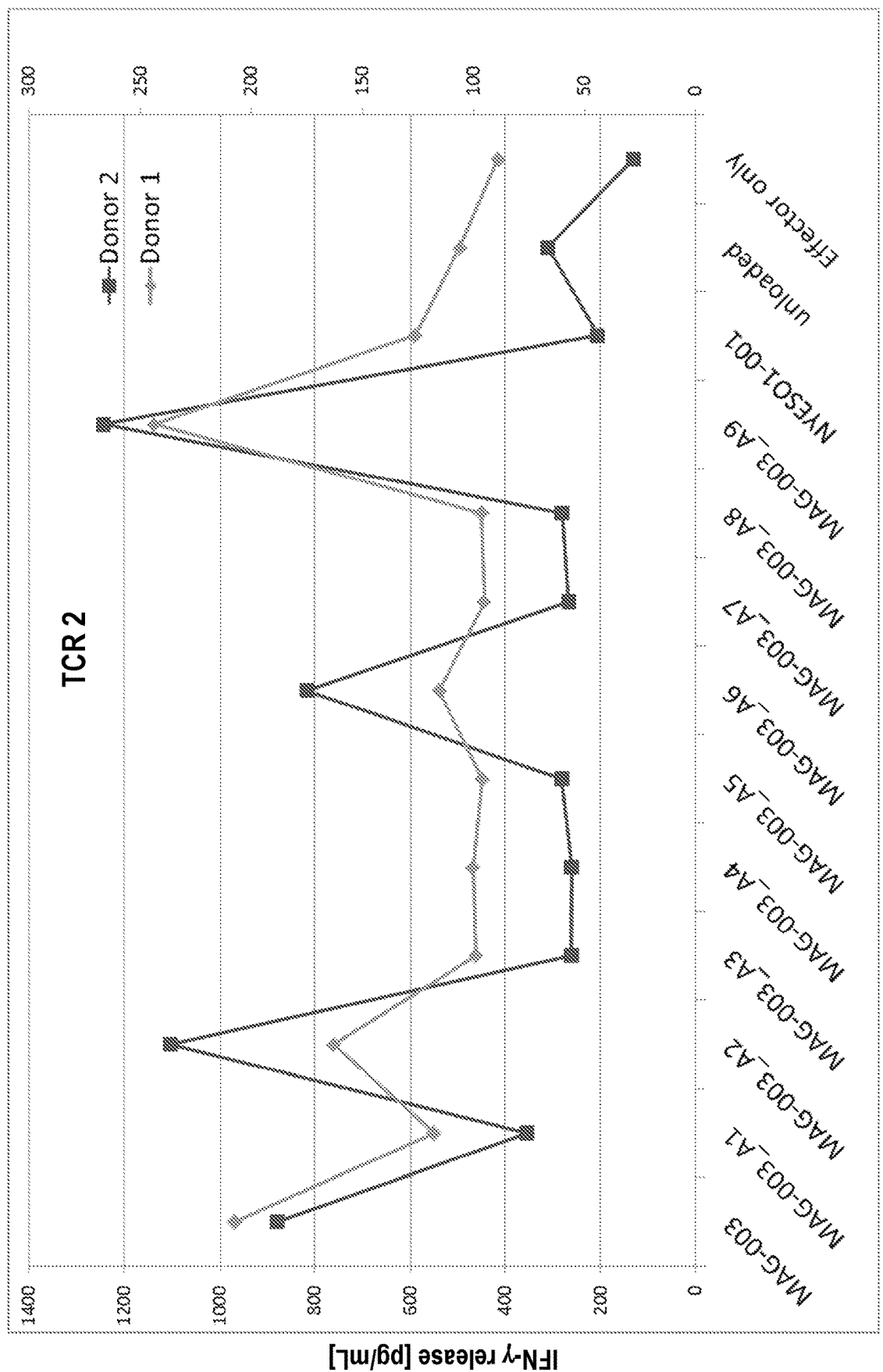
FIG. 4 shows IFNγ release from CD8+ T-cells electroporated with alpha and beta chain RNA of MAG-003 specific TCRs after co-incubation with target cells loaded with MAG-003 peptide (SEQ ID NO:1) or various MAG-003 alanine-substitution variants at positions 1-9 of SEQ ID NO:1 as disclosed herein.
Figure 5:
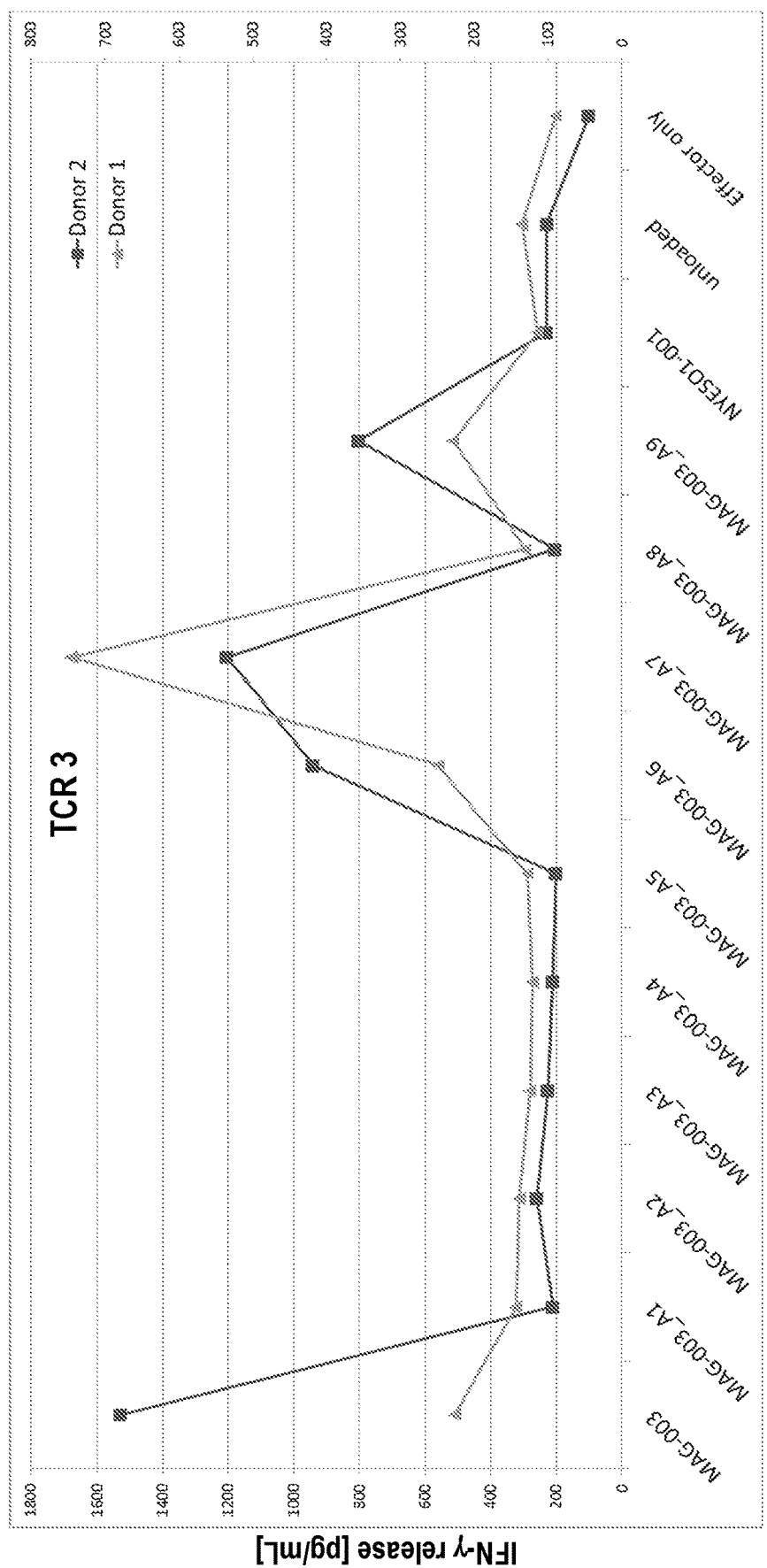
FIG. 5 shows IFNγ release from CD8+ T-cells electroporated with alpha and beta chain RNA of MAG-003 specific TCRs after co-incubation with target cells loaded with MAG-003 peptide (SEQ ID NO:1) or various MAG-003 alanine-substitution variants at positions 1-9 of SEQ ID NO:1 as disclosed herein.
Figure 6:
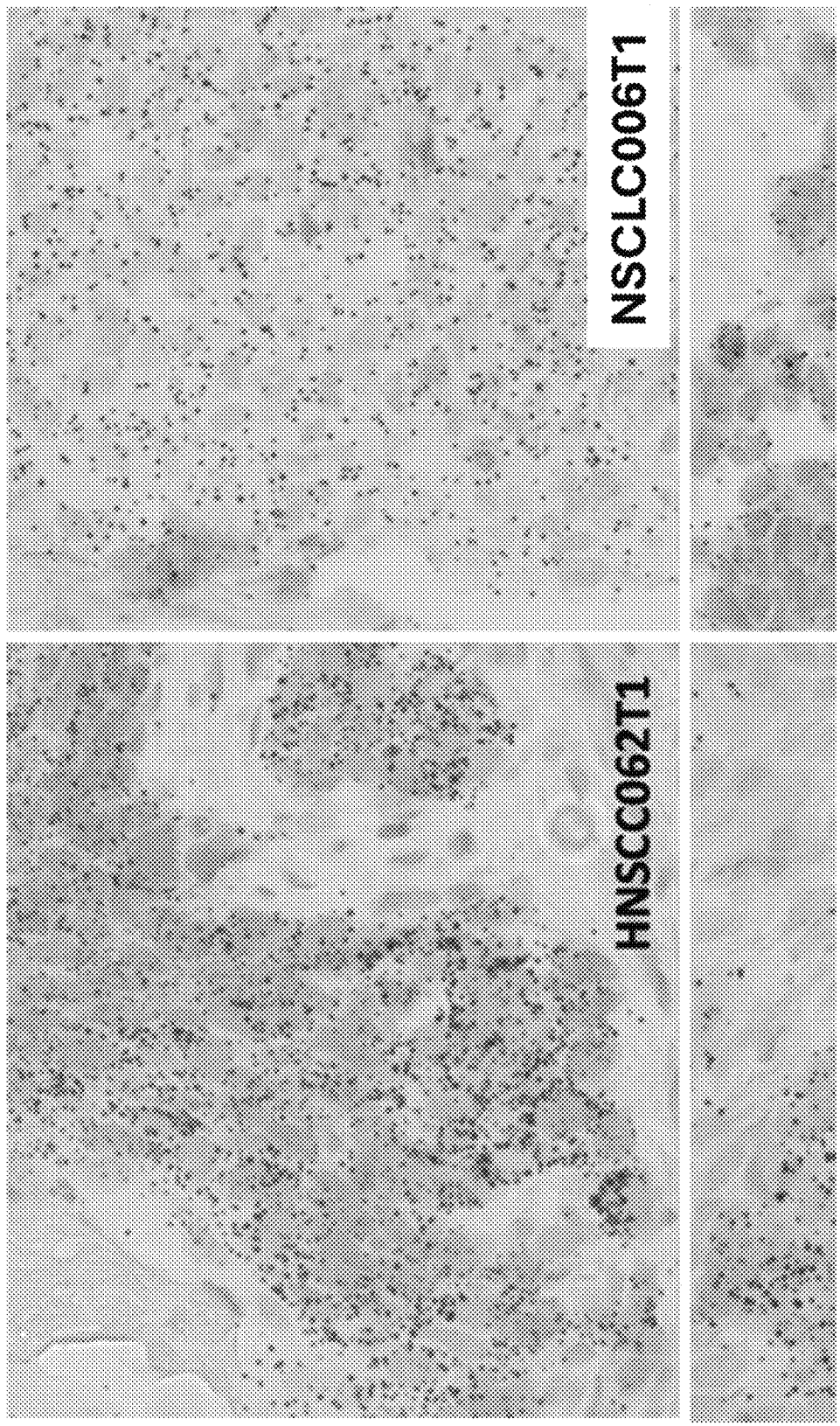
FIG. 6 shows MAGEA4 expression according to example 7. MAGEA4 mRNA is detectable in the presented cancer specimens. The level of expression covers a range from considerable expression in head and neck cancer and non-small lung cancer specimens (HNSCC062T1, HNSCC064T1 and NSCLC004T1) to rather low expression in non-small lung cancer and ovarian cancer specimens (NSCLC006T1 and OC036T1).

Allo-reactive settings can be used to circumvent self-tolerance and yield T-cells with a higher avidity when compared to T-cells derived from autologous settings, i.e., patients. Examples of such settings include in vitro generation of allo-HLA reactive, peptide-specific T-cells (Sadovnikova et al. 1998; Savage et al. 2004; Wilde et al. 2012), and immunization of mice transgenic for human-MHC or human TCR (Stanislawski et al. 2001; Li et al. 2010).

Example 1

In vitro generation of allo-HLA reactive, peptide-specific T-cells (Savage et al. 2004) PBMCs from HLA-A*02-negative healthy donors were used after obtaining informed consent. Recombinant biotinylated HLA-A2 class I monomers and A2 fluorescent tetramers containing MAG-003 were obtained from MBLI (Woburn, MA). PBMCs were incubated with anti-CD20SA diluted in phosphate buffered saline (PBS) for 1 hour at room temperature, washed, and incubated with the biotinylated A2/MAG-003 monomers for 30 minutes at room temperature, washed, and plated at 3×10$^6$ cells/well in 24-well plates in RPMI with 10% human AB serum. Interleukin 7 (IL-7; R&D Systems, Minneapolis, MN) was added on day 1 at 10 ng/mL and IL-2 (Chiron, Harefield, United Kingdom) was added at 10 U/mL on day 4. Over a 5-week period cells were restimulated weekly with fresh PBMCs, mixed with responder cells at a 1:1 ratio, and plated at 3×10$^6$/well in 24-well plates.

To obtain high avidity T-cells, incubate approximately 10$^6$ PBMCs with HLA-A2/MAG-003 tetramer-phycoerythrin (PE) (obtained from MBLI) for 30 minutes at 37° C., followed by anti-CD8-fluorescein isothiocyanate (FITC)/ allophycocyanin (APC) for 20 minutes at 4° C., followed by fluorescence activated cell sorting (FACS)-Calibur analysis.

Sorting was done with a FACS-Vantage (Becton Dickinson, Cowley, Oxford, United Kingdom). Sorted tetramer-positive cells were expanded in 24-well plates using, per well, $2 \times 10^5$ sorted cells, $2 \times 10^6$ irradiated A2-negative PBMCs as feeders, $2 \times 10^4$ CD3/CD28 beads/mL (Dynal, Oslo Norway), and IL-2 (1000 U/mL). The high avidity T-cells, thus obtained, were then be used to identify and isolate TCRs for amino acid/DNA sequences determination and cloning into expression vectors using methods well known in the art.

Example 2

Immunization of mice transgenic for human-MHC or human TCR

MAG-003 were used to immunize transgenic mice with the entire human TCRαβ gene loci (1.1 and 0.7 Mb), whose T-cells express a diverse human TCR repertoire that compensates for mouse TCR deficiency. (Li et al. 2010). To obtain high avidity T-cells, incubate PBMCs obtained from the transgenic mice with tetramer-phycoerythrin (PE) followed by cell sorting as described above. The high avidity T-cells, thus obtained, were then be used to identify and isolate TCRs for amino acid/DNA sequences determination and cloning into expression vectors using methods well known in the art.

In an aspect, MAG-003 and its variants, i.e., p286-1Y2L (having 2 amino acid substitutions, SEQ ID NO:2) and p286-1Y2L9L (having 3 amino acid substitutions, SEQ ID NO:3) exhibit potent binding affinity and stability towards HLA-A*0201 molecule. In particular, p286—1Y2L9L showed the capability to induce specific CTLs which, in an aspect, lyse the target cancer cells from both PBMCs of healthy donors and HLA-A2.1/Kb transgenic mice. See, for example, (Wu et al. 2011), the content of which is hereby incorporated by reference in its entirety.

To obtain high avidity TCRs for MHC I or II/p286-1Y2L or p286-1Y2L9L complexes, these peptides can be used in methods described in Examples 1 and 2. The high avidity T-cells, thus obtained, were then be used to identify and isolate TCRs for amino acid/DNA sequences determination and cloning into expression vectors using methods well known in the art.

High avidity TCR variants can also be selected from a library of CDR mutants by yeast, phage, or T-cell display (holler et al. 2003; Li et al. 2005; Chervin et al. 2008). Candidate TCR variants, thus, provide guidance to design mutations of the TCR's CDRs to obtain high avidity TCR variants (Robbins et al. 2008; Zoete et al. 2007).

Example 3: Cloning of TCRs

Methods of cloning TCRs are known in the art, for example, as described in U.S. Pat. No. 8,519,100, which is hereby incorporated by reference in its entirety for said methods. The alpha chain variable region sequence specific oligonucleotide A1 which encodes the restriction site NdeI, an introduced methionine for efficient initiation of expression in bacteria, and an alpha chain constant region sequence specific oligonucleotide A2 which encodes the restriction site SalI are used to amplify the alpha chain variable region. In the case of the beta chain, a beta chain variable region sequence specific oligonucleotide which encodes the restriction site e.g. NdeI, an introduced methionine for efficient initiation of expression in bacteria, and a beta chain constant region sequence specific oligonucleotide B2 which encodes the restriction site e.g. AgeI are used to amplify the beta chain variable region.

The alpha and beta variable regions were cloned into pGMT7-based expression plasmids containing either Cα or Cβ by standard methods described in (Molecular Cloning a Laboratory Manual Third edition by Sambrook and Russell). Plasmids were sequenced using an Applied Biosystems 3730×1 DNA Analyzer.

The DNA sequences encoding the TCR alpha chain cut with NdeI and SalI were ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI. Ligated plasmids are transformed into competent *Escherichia coli* strain XL1-blue cells and plated out on LB/agar plates containing 100 μg/ml ampicillin. Following incubation overnight at 37° C., single colonies are picked and grown in 10 ml LB containing 100 μg/ml ampicillin overnight at 37° C. with shaking. Cloned plasmids are purified using a Miniprep kit (Qiagen) and the insert is sequenced using an automated DNA sequencer (Lark Technologies).

Example 4: Autologous T-Cell Engineering

T-cells can be engineered to express high avidity TCRs (so-called TCR therapies) or protein-fusion derived chimeric antigen receptors (CARs) that have enhanced antigen specificity to MHC I/MAG-003 complex or MHC II/MAG-003 complex. In an aspect, this approach overcomes some of the limitations associated with central and peripheral tolerance, and generates T-cells that will be more efficient at targeting tumors without the requirement for de novo T-cell activation in the patient.

To obtain T-cells expressing TCRs of the present description, nucleic acids encoding the tumor specific TCR-alpha and/or TCR-beta chains identified and isolated, as described in Examples 1-3, were cloned into expression vectors, such as gamma-retrovirus or lentivirus. The recombinant viruses were generated and then tested for functionality, such as antigen specificity and functional avidity. An aliquot of the final product is then used to transduce the target T-cell population (generally purified from patient PBMCs), which is expanded before infusion into the patient.

TCR chains introduced into a peripheral T-cell may compete with endogenous TCR chains for association with the CD3 complex, which is necessary for TCR surface expression. Because a high level of TCR surface expression is essential to confer appropriate sensitivity for triggering by cells expressing the target tumor antigen (Cooper et al., 2000; Labrecque et al., 2001), strategies that enhance TCR-alpha and TCR-beta gene expression levels are an important consideration in TCR gene therapy.

To increase the expression of TCR of the present description, strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter (Cooper et al., 2004; Jones et al., 2009), elongation factor (EF)-1a (Tsuji et al., 2005) and the spleen focus-forming virus (SFFV) promoter (Joseph et al., 2008), can be used in the present description.

In addition to strong promoters, many TCR expression cassettes contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

Achieving high-level TCR surface expression requires that both the TCR-alpha and TCR-beta chains of the introduced TCR be transcribed at high levels. To do so, the TCR-alpha and TCR-beta chains of the present description may be cloned into bicistronic constructs in a single vector, which has been shown to be capable of overcoming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Another modification that has proven to be beneficial for increasing TCR transgene expression is codon optimization. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

The present description provides TCR proteins that are useful in treating cancers/tumors, preferably non-small cell lung cancer that over- or exclusively present MAG-003.

Example 5: Allogeneic T-Cell Engineering

Gamma delta (γδ) T cells, which are non-conventional T lymphocyte effectors implicated in the first line of defense against pathogens, can interact with and eradicate tumor cells in a MHC-independent manner through activating receptors, among others, TCR-gamma and TCR-delta chains. These γδ T cells display a preactivated phenotype that allows rapid cytokine production (IFN-γ, TNF-α) and strong cytotoxic response upon activation. These T-cells have anti-tumor activity against many cancers and suggest that γδ T cell-mediated immunotherapy is feasible and can induce objective tumor responses. (Braza et al. 2013).

Recent advances using immobilized antigens, agonistic monoclonal antibodies (mAbs), tumor-derived artificial antigen presenting cells (aAPC), or combinations of activating mAbs and aAPC have been successful in expanding gamma delta T-cells with oligoclonal or polyclonal TCR repertoires. For example, immobilized major histocompatibility complex Class-I chain-related A was a stimulus for γδ T-cells expressing TCRδ1 isotypes, and plate-bound activating antibodies have expanded Vδ1 and Vδ2 cells ex vivo. Clinically sufficient quantities of TCRδ1, TCRδ2, and TCRδ1$^{neg}$ TCRδ2$^{neg}$ have been produced following co-culture on aAPC, and these subsets displayed differences in memory phenotype and reactivity to tumors in vitro and in vivo. (Deniger et al. 2014).

In addition, γδ T-cells are amenable to genetic modification as evidenced by introduction of TCR-alpha and TCR-beta chains. (Hiasa et al. 2009). Another aspect of the present description relates to production of γδ T-cells expressing TCR-alpha and TCR-beta that bind to MAG-003. To do so, γδ T-cells are expanded by methods described by Deniger et al. 2014, followed by transducing the recombinant viruses expressing the TCRs that bind to MAG-003 (as described in Example 3) into the expanded γδ T-cells. The virus-transduced γδ T-cells are then infused into the patient.

Example 6: Immunogenicity and Functional T-Cell Data

The immunogenicity of MAG-003 was tested using protocols that mimic the manufacturing procedure for a pharmaceutical product. Priming of MAG-003-specific T-cells was observed for healthy donors. Generated T cells were able to kill peptide loaded target cells demonstrating their functionality. The data demonstrated that 1) MAG-003 is an immunogenic target and 2) that generated T cells against MAG-003 are functional.

Additional data as generated provided evidence that MAG-003 is a peptide with very good binding to HLA-A*02:01.

Example 7: MAGEA4 mRNa Expression in Tissues

In situ hybridization (ISH) is used to detect mRNA expression directly in formalin-fixed or frozen tissue sections. Due to its high sensitivity and its spatial resolution, it is a suitable method to determine cell type specific target expression and the distribution or frequency of target expression within cancer tissue sections.

ISH has been performed to detect MAGEA4 mRNA using the BaseScope™ technology developed by Advanced Cell Diagnostics (ACD). The BaseScope™ technology is based on the hybridization of on to four pairs of Z-shaped oligonucleotide probes to the target sequence. Signal amplification is achieved by branched DNA amplification, which is based on multiple hybridization steps of oligonucleotides, ultimately building up a branched DNA (bDNA) tree. Finally, a great number of label probes hybridize to the branches of the bDNA tree and the enhanced signal can be detected. The chromogenic BaseScope™ Detection Kit (RED) includes label probes which are linked to an enzyme (alkaline phosphatase). Signal detection depends on the enzymatic conversion of the chromogenic substrate FastRed, which additionally amplifies the original signal. BaseScope™ is a very sensitive technology, which is due to the efficient process of signal amplification, paired with the high sensitivity and the robust binding of the Z probe pairs to the target mRNA, even if it is partially crosslinked or degraded. According to ACD, binding of one single probe pair to each single mRNA molecule is enough to generate a detectable ISH signal.

Each ISH experiment is subdivided into two methodological processes: 1) Tissue pretreatment for target retrieval, and 2) Target hybridization, signal amplification and detection. Optimal pretreatment conditions are critical for successful target detection in FFPE tissue sections. The fixation process induces crosslinking of proteins, DNA and RNA in cells and tissues and thereby masks hybridization sites. Thus, to assure accessibility of the target mRNA and proper binding of the probe set, these crosslinks have to be removed prior to target hybridization. Tissue pretreatment includes three discrete steps: 1) Blocking of endogenous alkaline phosphatase by hydrogen peroxide treatment, 2) target retrieval by boiling in target retrieval reagent, and 3) target retrieval by protease digestion. As the extent of fixation and crosslinking may vary between different FFPE blocks, the optimal target retrieval conditions have to be determined experimentally for each individual FFPE block. Therefore, tissue sections were exposed to different boiling and protease digestion times followed by hybridization with a positive and a negative control probe set. The optimal conditions were determined by microscopic evaluation of specific signal intensity in the positive control, unspecific background in the negative control and tissue morphology. Tissue pre-treatment was performed according to the manufacturer's protocols. Pretreatment reagents are included in the BaseScope™ reagent kits. After completion of the different pretreatment steps, target expression was assessed by hybridization of specific probe sets to the mRNA of interest with subsequent branched DNA signal amplification and chromogenic or fluorescent signal detection. All assays were performed according to the manufacturer's protocols.

TABLE 10

Expression analysis

| Sample | Tissue | MAGEA4 expression |
|---|---|---|
| HNSCC062T1 | Head and neck cancer | ++ |
| HNSCC064T1 | Head and neck cancer | ++ |
| NSCLC004T1 | Non-small cell lung cancer | ++ |
| NSCLC006T1 | Non-small cell lung cancer | + |
| OC036T1 | Ovarian cancer | + |

Overall expression level of MAGEA4 in the respective section: ± very low, + low to moderate, ++ strong, +++ very strong

REFERENCE LIST

Adair S J, Hogan K T (2009). Treatment of ovarian cancer cell lines with 5-aza-2'-deoxycytidine upregulates the expression of cancer-testis antigens and class I major histocompatibility complex-encoded molecules. Cancer Immunol. Immunother. 58, 589-601.

Alves P M, Levy N, Bouzourene H, Viatte S, Bricard G, Ayyoub M, Vuilleumier H, Givel J C, Halkic N, Speiser D E, Romero P, Levy F (2007). Molecular and immunological evaluation of the expression of cancer/testis gene products in human colorectal cancer. Cancer Immunol. Immunother. 56, 839-847.

Andrade V C, Vettore A L, Felix R S, Almeida M S, Carvalho F, Oliveira J S, Chauffaille M L, Andriolo A, Caballero O L, Zago M A, Colleoni G W (2008). Prognostic impact of cancer/testis antigen expression in advanced stage multiple myeloma patients. Cancer Immun. 8, 2.

Aubry F, Satie A P, Rioux-Leclercq N, Rajpert-De M E, Spagnoli G C, Chomez P, De B O, Jegou B, Samson M (2001). MAGE-A4, a germ cell specific marker, is expressed differentially in testicular tumors. Cancer 92, 2778-2785.

Bar-Haim E, Paz A, Machlenkin A, Hazzan D, Tirosh B, Carmon L, Brenner B, Vadai E, Mor O, Stein A, Lemonnier F A, Tzehoval E, Eisenbach L (2004). MAGE-A8 overexpression in transitional cell carcinoma of the bladder: identification of two tumour-associated antigen peptides. Br. J Cancer 91, 398-407.

Barrow C, Browning J, MacGregor D, Davis I D, Sturrock S, Jungbluth A A, Cebon J (2006). Tumor antigen expression in melanoma varies according to antigen and stage. Clin Cancer Res 12, 764-771.

Bellati F, Napoletano C, Tarquini E, Palaia I, Landi R, Manci N, Spagnoli G, Rughetti A, Panici P B, Nuti M (2007). Cancer testis antigen expression in primary and recurrent vulvar cancer: association with prognostic factors. Eur. J Cancer 43, 2621-2627.

Bergeron A, Picard V, LaRue H, Harel F, Hovington H, Lacombe L, Fradet Y (2009). High frequency of MAGE-A4 and MAGE-A9 expression in high-risk bladder cancer. Int. J Cancer 125, 1365-1371.

Bhan S, Chuang A, Negi S S, Glazer C A, Califano J A (2012). MAGEA4 induces growth in normal oral keratinocytes by inhibiting growth arrest and apoptosis. Oncol Rep. 28, 1498-1502.

Bode P K, Thielken A, Brandt S, Barghorn A, Lohe B, Knuth A, Moch H (2014). Cancer testis antigen expression in testicular germ cell tumorigenesis. Mod. Pathol. 27, 899-905.

Cabezon T, Gromova I, Gromov P, Serizawa R, Timmermans W, V, Kroman N, Celis J E, Moreira J M (2013). Proteomic profiling of triple-negative breast carcinomas in combination with a three-tier orthogonal technology approach identifies Mage-A4 as potential therapeutic target in estrogen receptor negative breast cancer. Mol. Cell Proteomics. 12, 381-394.

Cesson V, Rivals J P, Escher A, Piotet E, Thielemans K, Posevitz V, Dojcinovic D, Monnier P, Speiser D, Bron L, Romero P (2011). MAGE-A3 and MAGE-A4 specific CD4(+) T-cells in head and neck cancer patients: detection of naturally acquired responses and identification of new epitopes. Cancer Immunol. Immunother. 60, 23-35.

Chambost H, Van B N, Brasseur F, Godelaine D, Xerri L, Landi S J, Theate I, Plumas J, Spagnoli G C, Michel G, Coulie P G, Olive D (2000). Expression of gene MAGE-A4 in Reed-Sternberg cells. Blood 95, 3530-3533.

Chen C H, Huang G T, Lee H S, Yang P M, Yan M D, Chen D S, Sheu J C (1999). High frequency of expression of MAGE genes in human hepatocellular carcinoma. 1999. Liver 19, 110-114.

Chitale D A, Jungbluth A A, Marshall D S, Leitao M M, Hedvat C V, Kolb D, Spagnoli G C, Iversen K, Soslow R A (2005). Expression of cancer-testis antigens in endometrial carcinomas using a tissue microarray. Mod. Pathol. 18, 119-126.

Coral S, Parisi G, Nicolay H J, Colizzi F, Danielli R, Fratta E, Covre A, Taverna P, Sigalotti L, Maio M (2013). Immunomodulatory activity of SGI–110, a 5-aza-2'-deoxycytidine-containing demethylating dinucleotide. Cancer Immunol. Immunother. 62, 605-614.

Cruz C R, Gerdemann U, Leen A M, Shafer J A, Ku S, Tzou B, Horton T M, Sheehan A, Copeland A, Younes A, Rooney C M, Heslop H E, Bollard C M (2011). Improving T-cell therapy for relapsed EBV-negative Hodgkin lymphoma by targeting upregulated MAGE-A4. Clin Cancer Res 17, 7058-7066.

Cuffel C, Rivals J P, Zaugg Y, Salvi S, Seelentag W, Speiser D E, Lienard D, Monnier P, Romero P, Bron L, Rimoldi D (2011). Pattern and clinical significance of cancer-testis gene expression in head and neck squamous cell carcinoma. Int. J Cancer 128, 2625-2634.

Daudi S, Eng K H, Mhawech-Fauceglia P, Morrison C, Miliotto A, Beck A, Matsuzaki J, Tsuji T, Groman A, Gnjatic S, Spagnoli G, Lele S, Odunsi K (2014). Expression and immune responses to MAGE antigens predict survival in epithelial ovarian cancer. PLoS. ONE. 9, e104099.

Duffour M T, Chaux P, Lurquin C, Cornelis G, Boon T, van der Bruggen P (1999). A MAGE-A4 peptide presented by HLA-A2 is recognized by cytolytic T lymphocytes. Eur. J Immunol. 29, 3329-3337.

De P E, Arden K, Traversari C, Gaforio J J, Szikora J P, De S C, Brasseur F, van der Bruggen P, Lethe B, Lurquin C, (1994). Structure, chromosomal localization, and expression of 12 genes of the MAGE family. Immunogenetics 40, 360-369.

Doyle J M, Gao J, Wang J, Yang M, Potts P R (2010). MAGE-RING protein complexes comprise a family of E3 ubiquitin ligases. Mol Cell 39, 963-974.

Eng K H, Weir I, Tsuji T, Odunsi K (2015). Immunostimulatory/regulatory gene expression patterns in advanced ovarian cancer. Genes and Cancer.

Forghanifard M M, Gholamin M, Farshchian M, Moaven O, Memar B, Forghani M N, Dadkhah E, Naseh H, Moghbeli M, Raeisossadati R, Abbaszadegan M R (2011). Cancer-testis gene expression profiling in esophageal squamous cell carcinoma: identification of specific tumor marker and potential targets for immunotherapy. Cancer Biol Ther. 12, 191-197.

Gerdemann U, Katari U, Christin A S, Cruz C R, Tripic T, Rousseau A, Gottschalk S M, Savoldo B, Vera J F, Heslop H E, Brenner M K, Bollard C M, Rooney C M, Leen A M (2011). Cytotoxic T lymphocytes simultaneously targeting multiple tumor-associated antigens to treat EBV negative lymphoma. Mol. Ther. 19, 2258-2268.

Gunda V, Cogdill A P, Bernasconi M J, Wargo J A, Parangi S (2013). Potential role of 5-aza-2'-deoxycytidine induced MAGE-A4 expression in immunotherapy for anaplastic thyroid cancer. Surgery 154, 1456-1462.

Gure A O, Chua R, Williamson B, Gonen M, Ferrera C A, Gnjatic S, Ritter G, Simpson A J, Chen Y T, Old L J, Altorki N K (2005). Cancer-testis genes are coordinately expressed and are markers of poor outcome in non-small cell lung cancer. Clin Cancer Res 11, 8055-8062.

Hartmann S, Meyer T J, Brands R C, Haubitz I R, Linz C, Seher A, Kubler A C, Muller-Richter U D (2015). MAGE-A expression clusters and antineoplastic treatment in head and neck cancer. Int. J Mol. Med. 35, 1675-1682.

Hasegawa H, Mori M, Haraguchi M, Ueo H, Sugimachi K, Akiyoshi T (1998). Expression spectrum of melanoma antigen-encoding gene family members in colorectal carcinoma. Arch. Pathol. Lab Med. 122, 551-554.

Hussein Y M, Morad F E, Gameel M A, Emam W A, El Sawy W H, El Tarhouny S A, Bayomy E S, Raafat N (2012). MAGE-4 gene m-RNA and TGF in blood as potential biochemical markers for HCC in HCV-infected patients. Med. Oncol 29, 3055-3062.

Jacobs J F, Grauer O M, Brasseur F, Hoogerbrugge P M, Wesseling P, Gidding C E, van de Rakt M W, Figdor C G, Coulie P G, de Vries I J, Adema G J (2008). Selective cancer-germline gene expression in pediatric brain tumors. J Neurooncol. 88, 273-280.

Jia Z C, Ni B, Huang Z M, Tian Y, Tang J, Wang J X, Fu X L, Wu Y Z (2010). Identification of two novel HLA-A*0201-restricted CTL epitopes derived from MAGE-A4. Clin Dev. Immunol. 2010, 567594.

Kageyama S, Ikeda H, Miyahara Y, Imai N, Ishihara M, Saito K, Sugino S, Ueda S, Ishikawa T, Kokura S, Naota H, Ohishi K, Shiraishi T, Inoue N, Tanabe M, Kidokoro T, Yoshioka H, Tomura D, Nukaya I, Mineno J, Takesako K, Katayama N, Shiku H (2015). Adoptive Transfer of MAGE-A4 T-cell Receptor Gene-Transduced Lymphocytes in Patients with Recurrent Esophageal Cancer. Clin. Cancer Res.

Kang J, Lee H J, Kim J, Lee J J, Maeng L S (2015). Dysregulation of X chromosome inactivation in high grade ovarian serous adenocarcinoma. PLoS. ONE. 10, e0118927.

Kawagoe H, Yamada A, Matsumoto H, Ito M, Ushijima K, Nishida T, Yakushiji M, Itoh K (2000). Serum MAGE-4 protein in ovarian cancer patients. Gynecol. Oncol 76, 336-339.

Kim K, Cho Y M, Park B H, Lee J L, Ro J Y, Go H, Shim J W (2015). Histological and immunohistochemical markers for progression prediction in transurethrally resected high-grade non-muscle invasive bladder cancer. Int. J Clin Exp. Pathol. 8, 743-750.

Kobayashi T, Lonchay C, Colau D, Demotte N, Boon T, van der Bruggen P (2003). New MAGE-4 antigenic peptide recognized by cytolytic T lymphocytes on HLA-A1 tumor cells. Tissue Antigens 62, 426-432.

Kocher T, Zheng M, Bolli M, Simon R, Forster T, Schultz-Thater E, Remmel E, Noppen C, Schmid U, Ackermann D, Mihatsch M J, Gasser T, Heberer M, Sauter G, Spagnoli G C (2002). Prognostic relevance of MAGE-A4 tumor antigen expression in transitional cell carcinoma of the urinary bladder: a tissue microarray study. Int. J Cancer 100, 702-705.

Kubuschok B, Xie X, Jesnowski R, Preuss K D, Romeike B F, Neumann F, Regitz E, Pistorius G, Schilling M, Scheunemann P, Izbicki J R, Lohr J M, Pfreundschuh M (2004). Expression of cancer testis antigens in pancreatic carcinoma cell lines, pancreatic adenocarcinoma and chronic pancreatitis. Int. J Cancer 109, 568-575.

Li J, Yang Y, Fujie T, Tanaka F, Mimori K, Haraguchi M, Ueo H, Mori M, Akiyoshi T (1997). Expression of the MAGE gene family in human gastric carcinoma. Anticancer Res 17, 3559-3563.

Li M, Yuan Y H, Han Y, Liu Y X, Yan L, Wang Y, Gu J (2005). Expression profile of cancer-testis genes in 121 human colorectal cancer tissue and adjacent normal tissue. Clin Cancer Res 11, 1809-1814.

Lifantseva N, Koltsova A, Krylova T, Yakovleva T, Poljanskaya G, Gordeeva O (2011). Expression patterns of cancer-testis antigens in human embryonic stem cells and their cell derivatives indicate lineage tracks. Stem Cells Int. 2011, 795239.

Luftl M, Schuler G, Jungbluth A A (2004). Melanoma or not? Cancer testis antigens may help. Br. J Dermatol. 151, 1213-1218.

Lin J, Lin L, Thomas D G, Greenson J K, Giordano T J, Robinson G S, Barve R A, Weishaar F A, Taylor J M, Orringer M B, Beer D G (2004). Melanoma-associated antigens in esophageal adenocarcinoma: identification of novel MAGE-A10 splice variants. Clin Cancer Res 10, 5708-5716.

Liu W, Cheng S, Asa S L, Ezzat S (2008). The melanoma-associated antigen A3 mediates fibronectin-controlled cancer progression and metastasis. Cancer Res 68, 8104-8112.

Marcar L, Ihrig B, Hourihan J, Bray S E, Quinlan P R, Jordan L B, Thompson A M, Hupp T R, Meek D W (2015). MAGE-A Cancer/Testis Antigens Inhibit MDM2 Ubiquitylation Function and Promote Increased Levels of MDM4. PLoS. ONE. 10, e0127713.

Marcar L, Maclaine N J, Hupp T R, Meek D W (2010a). Mage-A cancer/testis antigens inhibit p53 function by blocking its interaction with chromatin. Cancer Res 70, 10362-10370.

Marcar L, Maclaine N J, Hupp T R, Meek D W (2010b). Mage-A cancer/testis antigens inhibit p53 function by blocking its interaction with chromatin. Cancer Res 70, 10362-10370.

Melo D H, Mamede R C, Neder L, Saggioro F P, Figueiredo D L, da Silva W A J, Jungbluth A A, Zago M A (2011). Expression of MAGE-A4 and MAGE-C1 tumor-associated antigen in benign and malignant thyroid diseases. Head Neck 33, 1426-1432.

Mischo A, Kubuschok B, Ertan K, Preuss K D, Romeike B, Regitz E, Schormann C, de B D, Wadle A, Neumann F, Schmidt W, Renner C, Pfreundschuh M (2006). Prospective study on the expression of cancer testis genes and antibody responses in 100 consecutive patients with primary breast cancer. Int. J Cancer 118, 696-703.

Mitchell R T, Camacho-Moll E, MacDonald J, Anderson R A, Kelnar C J, O'Donnell M, Sharpe R M, Smith L B, Grigor K M, Wallace W H, Stoop H, Wolffenbuttel K P, Donat R, Saunders P T, Looijenga L H (2014). Intratubular germ cell neoplasia of the human testis: heterogeneous protein expression and relation to invasive potential. Mod. Pathol. 27, 1255-1266.

Miyahara Y, Naota H, Wang L, Hiasa A, Goto M, Watanabe M, Kitano S, Okumura S, Takemitsu T, Yuta A, Majima Y, Lemonnier F A, Boon T, Shiku H (2005). Determination of cellularly processed novel HLA-A2402-restricted novel CTL epitopes derived from two cancer germ line genes, MAGE-A4 and SAGE. Clin Cancer Res 11, 5581-5589.

Montoro J R, Mamede R C, Neder S L, Saggioro F P, Figueiredo D L, Silva W A, Jr., Jungbluth A A, Spagnoli G C, Zago M A (2012). Expression of cancer-testis antigens MAGE-A4 and MAGE-C1 in oral squamous cell carcinoma. Head Neck 34, 1123-1128.

Monte M, Simonatto M, Peche L Y, Bublik D R, Gobessi S, Pierotti M A, Rodolfo M, Schneider C (2006). MAGE-A tumor antigens target p53 transactivation function through histone deacetylase recruitment and confer resistance to chemotherapeutic agents. Proc. Natl. Acad. Sci. U.S.A 103, 11160-11165.

Nagao T, Higashitsuji H, Nonoguchi K, Sakurai T, Dawson S, Mayer R J, Itoh K, Fujita J (2003). MAGE-A4 interacts with the liver oncoprotein gankyrin and suppresses its tumorigenic activity. J Biol Chem 278, 10668-10674.

Naota H, Miyahara Y, Okumura S, Kuzushima K, Akatsuka Y, Hiasa A, Kitano S, Takahashi T, Yuta A, Majima Y, Shiku H (2006). Generation of peptide-specific CD8+ T-cells by phytohemagglutinin-stimulated antigen-mRNA-transduced CD4+ T-cells. J Immunol. Methods 314, 54-66.

Nishikawa H, Maeda Y, Ishida T, Gnjatic S, Sato E, Mori F, Sugiyama D, Ito A, Fukumori Y, Utsunomiya A, Inagaki H, Old L J, Ueda R, Sakaguchi S (2012). Cancer/testis antigens are novel targets of immunotherapy for adult T-cell leukemia/lymphoma. Blood 119, 3097-3104.

Nishimura S, Fujita M, Terata N, Tani T, Kodama M, Itoh K (1997). Expression of MAGE genes in colorectal carcinomas. Nihon Rinsho Meneki. Gakkai Kaishi 20, 95-101.

Oba-Shinjo S M, Caballero O L, Jungbluth A A, Rosemberg S, Old L J, Simpson A J, Marie S K (2008). Cancer-testis (CT) antigen expression in medulloblastoma. Cancer Immun. 8, 7.

Ohkuri T, Wakita D, Chamoto K, Togashi Y, Kitamura H, Nishimura T (2009).

Identification of novel helper epitopes of MAGE-A4 tumor antigen: useful tool for the propagation of Th1 cells. Br. J Cancer 100, 1135-1143.

Ottaviani S, Colau D, van der Bruggen P, van der Bruggen P (2006). A new MAGE-4 antigenic peptide recognized by cytolytic T lymphocytes on HLA-A24 carcinoma cells. Cancer Immunol. Immunother. 55, 867-872.

Otte M, Zafrakas M, Riethdorf L, Pichlmeier U, Loning T, Janicke F, Pantel K (2001). MAGE-A gene expression pattern in primary breast cancer. Cancer Res 61, 6682-6687.

Peikert T, Specks U, Farver C, Erzurum S C, Comhair S A (2006). Melanoma antigen A4 is expressed in non-small cell lung cancers and promotes apoptosis. Cancer Res 66, 4693-4700.

Peng J R, Chen H S, Mou D C, Cao J, Cong X, Qin L L, Wei L, Leng X S, Wang Y, Chen W F (2005). Expression of cancer/testis (CT) antigens in Chinese hepatocellular carcinoma and its correlation with clinical parameters. Cancer Lett. 219, 223-232.

Perez D, Herrmann T, Jungbluth A A, Samartzis P, Spagnoli G, Demartines N, Clavien P A, Marino S, Seifert B, Jaeger D (2008). Cancer testis antigen expression in gastrointestinal stromal tumors: new markers for early recurrence. Int. J Cancer 123, 1551-1555.

Prasad M L, Jungbluth A A, Patel S G, Iversen K, Hoshaw-Woodard S, Busam K J (2004). Expression and significance of cancer testis antigens in primary mucosal melanoma of the head and neck. Head Neck 26, 1053-1057.

Quillien V, Raoul J L, Heresbach D, Collet B, Toujas L, Brasseur F (1997). Expression of MAGE genes in esophageal squamous-cell carcinoma. Anticancer Res. 17, 387-391.

Rammensee H G, Bachmann J, Emmerich N P, Bachor O A, Stevanovic S (1999). SYFPEITHI: database for MHC ligands and peptide motifs. Immunogenetics 50, 213-219.

Rammensee H G, Bachmann J, Stevanovic S (1997). MHC Ligands and Peptide Motifs. (Heidelberg, Germany: Springer-Verlag).

Resnick M B, Sabo E, Kondratev S, Kerner H, Spagnoli G C, Yakirevich E (2002). Cancer-testis antigen expression in uterine malignancies with an emphasis on carcinosarcomas and papillary serous carcinomas. Int. J Cancer 101, 190-195.

Ries J, Schultze-Mosgau S, Neukam F, Diebel E, Wiltfang J (2005). Investigation of the expression of melanoma antigen-encoding genes (MAGE-A1 to -A6) in oral squamous cell carcinomas to determine potential targets for gene-based cancer immunotherapy. Int. J Oncol. 26, 817-824.

Roch N, Kutup A, Vashist Y, Yekebas E, Kalinin V, Izbicki J R (2010). Coexpression of MAGE-A peptides and HLA class I molecules in hepatocellular carcinoma. Anticancer Res 30, 1617-1623.

Saito T, Wada H, Yamasaki M, Miyata H, Nishikawa H, Sato E, Kageyama S, Shiku H, Mori M, Doki Y (2014). High expression of MAGE-A4 and MHC class I antigens in tumor cells and induction of MAGE-A4 immune responses are prognostic markers of CHP-MAGE-A4 cancer vaccine. Vaccine 32, 5901-5907.

Sakurai T, Itoh K, Higashitsuji H, Nagao T, Nonoguchi K, Chiba T, Fujita J (2004). A cleaved form of MAGE-A4 binds to Miz-1 and induces apoptosis in human cells. J Biol Chem 279, 15505-15514.

Sarcevic B, Spagnoli G C, Terracciano L, Schultz-Thater E, Heberer M, Gamulin M, Krajina Z, Oresic T, Separovic R, Juretic A (2003). Expression of cancer/testis tumor associated antigens in cervical squamous cell carcinoma. Oncology 64, 443-449.

Schirmer U, Fiegl H, Pfeifer M, Zeimet A G, Muller-Holzner E, Bode P K, Tischler V, Altevogt P (2013). Epigenetic regulation of L1CAM in endometrial carcinoma: comparison to cancer-testis (CT-X) antigens. BMC. Cancer 13, 156.

Shafer J A, Cruz C R, Leen A M, Ku S, Lu A, Rousseau A, Heslop H E, Rooney C M, Bollard C M, Foster A E (2010). Antigen-specific cytotoxic T lymphocytes can target chemoresistant side-population tumor cells in Hodgkin lymphoma. Leuk. Lymphoma 51, 870-880.

Sharma P, Shen Y, Wen S, Bajorin D F, Reuter V E, Old L J, Jungbluth A A (2006). Cancer-testis antigens: expression and correlation with survival in human urothelial carcinoma. Clin Cancer Res 12, 5442-5447.

Shichijo S, Hoshino T, Koufuji K, Hayashi A, Kawamoto M, Kikuchi M, Higuchi T, Ichiki M, Oizumi K, Itoh K (1997). Detection of MAGE-4 protein in sera of lung cancer patients. Jpn. J Cancer Res 88, 414-419.

Shigematsu Y, Hanagiri T, Shiota H, Kuroda K, Baba T, Mizukami M, So T, Ichiki Y, Yasuda M, So T, Takenoyama M, Yasumoto K (2010). Clinical significance of cancer/testis antigens expression in patients with non-small cell lung cancer. Lung Cancer 68, 105-110.

Shirakura Y, Mizuno Y, Wang L, Imai N, Amaike C, Sato E, Ito M, Nukaya I, Mineno J, Takesako K, Ikeda H, Shiku H (2012). T-cell receptor gene therapy targeting melanoma-associated antigen-A4 inhibits human tumor growth in non-obese diabetic/SCID/gammacnull mice. Cancer Sci. 103, 17-25.

Simpson A J, Caballero O L, Jungbluth A, Chen Y T, Old L J (2005). Cancer/testis antigens, gametogenesis and cancer. Nat Rev. Cancer 5, 615-625.

Soga N, Hori Y, Yamakado K, Ikeda H, Imai N, Kageyama S, Nakase K, Yuta A, Hayashi N, Shiku H, Sugimura Y (2013). Limited expression of cancer-testis antigens in renal cell carcinoma patients. Mol. Clin Oncol 1, 326-330.

Su C, Xu Y, Li X, Ren S, Zhao C, Hou L, Ye Z, Zhou C (2015). Predictive and prognostic effect of CD133 and cancer-testis antigens in stage Ib-IIIA non-small cell lung cancer. Int. J Clin Exp. Pathol. 8, 5509-5518.

Takahashi N, Ohkuri T, Homma S, Ohtake J, Wakita D, Togashi Y, Kitamura H, Todo S, Nishimura T (2012). First clinical trial of cancer vaccine therapy with artificially synthesized helper/killer-hybrid epitope long peptide of MAGE-A4 cancer antigen. Cancer Sci. 103, 150-153.

Tahara K, Mori M, Sadanaga N, Sakamoto Y, Kitano S, Makuuchi M (1999b). Expression of the MAGE gene family in human hepatocellular carcinoma 1999. Cancer 85, 1234-1240.

Tanaka F, Mori M, Li J, Fujie T, Mimori K, Haraguchi M, Tanaka Y, Mafune K, Akiyoshi T (1997). High frequency of the expression of the MAGE gene family in human esophageal carcinoma. Int. J Oncol 10, 1113-1117.

Tsuzurahara S, Sata M, Iwamoto O, Shichijo S, Kojiro M, Tanikawa K, Itoh K (1997). Detection of MAGE-4 protein in the sera of patients with hepatitis-C virus-associated hepatocellular carcinoma and liver cirrhosis. Jpn. J Cancer Res 88, 915-918.

Wang M, Li J, Wang L, Chen X, Zhang Z, Yue D, Ping Y, Shi X, Huang L, Zhang T, Yang L, Zhao Y, Ma X, Li D, Fan Z, Zhao L, Tang Z, Zhai W, Zhang B, Zhang Y (2015). Combined cancer testis antigens enhanced prediction accuracy for prognosis of patients with hepatocellular carcinoma. Int. J Clin Exp. Pathol. 8, 3513-3528.

Wilson E M (2010). Androgen receptor molecular biology and potential targets in prostate cancer. Ther. Adv. Urol. 2, 105-117.

Wolff A C, Hammond M E, Hicks D G, Dowsett M, McShane L M, Allison K H, Allred D C, Bartlett J M, Bilous M, Fitzgibbons P, Hanna W, Jenkins R B, Mangu P B, Paik S, Perez E A, Press M F, Spears P A, Vance G H, Viale G, Hayes D F (2013). Recommendations for human epidermal growth factor receptor 2 testing in breast cancer: American Society of Clinical Oncology/College of American Pathologists clinical practice guideline update. J Clin Oncol 31, 3997-4013.

Wong P P, Yeoh C C, Ahmad A S, Chelala C, Gillett C, Speirs V, Jones J L, Hurst H C (2014). Identification of MAGEA antigens as causal players in the development of tamoxifen-resistant breast cancer. Oncogene 33, 4579-4588.

Wu Z Y, Gao Y F, Wu Y H, Liu W, Sun M, Zhai M X, Qi Y M, Ye Y (2011). Identification of a novel CD8+ T-cell epitope derived from cancer-testis antigen MAGE-4 in oesophageal carcinoma. Scand. J Immunol. 74, 561-567.

Yakirevich E, Sabo E, Lavie O, Mazareb S, Spagnoli G C, Resnick M B (2003). Expression of the MAGE-A4 and NY-ESO-1 cancer-testis antigens in serous ovarian neoplasms. Clin Cancer Res 9, 6453-6460.

Yang B, O'Herrin S M, Wu J, Reagan-Shaw S, Ma Y, Bhat K M, Gravekamp C, Setaluri V, Peters N, Hoffmann F M, Peng H, Ivanov A V, Simpson A J, Longley B J (2007). MAGE-A, mMage-b, and MAGE-C proteins form complexes with KAP1 and suppress p53-dependent apoptosis in MAGE-positive cell lines. Cancer Res 67, 9954-9962.

Yamada R, Takahashi A, Torigoe T, Morita R, Tamura Y, Tsukahara T, Kanaseki T, Kubo T, Watarai K, Kondo T, Hirohashi Y, Sato N (2013). Preferential expression of cancer/testis genes in cancer stem-like cells: proposal of a novel sub-category, cancer/testis/stem gene. Tissue Antigens 81, 428-434.

Yoshida N, Abe H, Ohkuri T, Wakita D, Sato M, Noguchi D, Miyamoto M, Morikawa T, Kondo S, Ikeda H, Nishimura T (2006). Expression of the MAGE-A4 and NY-ESO-1 cancer-testis antigens and T-cell infiltration in non-small cell lung carcinoma and their prognostic significance. Int. J Oncol 28, 1089-1098.

Zhang Y, Stroobant V, Russo V, Boon T, van der Bruggen P (2002). A MAGE-A4 peptide presented by HLA-B37 is recognized on human tumors by cytolytic T lymphocytes. Tissue Antigens 60, 365-371.

Zimmermann A K, Imig J, Klar A, Renner C, Korol D, Fink D, Stadlmann S, Singer G, Knuth A, Moch H, Caduff R (2013). Expression of MAGE-C1/CT7 and selected cancer/testis antigens in ovarian borderline tumours and primary and recurrent ovarian carcinomas. Virchows Arch. 462, 565-574.

```
                               SEQUENCE LISTING

Sequence total quantity: 25
SEQ ID NO: 1            moltype = AA  length = 9
FEATURE                 Location/Qualifiers
source                  1..9
                        mol_type = protein
                        organism = Homo sapiens
SEQUENCE: 1
KVLEHVVRV                                                                  9

SEQ ID NO: 2            moltype = AA  length = 9
FEATURE                 Location/Qualifiers
source                  1..9
                        mol_type = protein
                        organism = Homo sapiens
SEQUENCE: 2
KVLEHVVRL                                                                  9

SEQ ID NO: 3            moltype = AA  length = 9
FEATURE                 Location/Qualifiers
source                  1..9
                        mol_type = protein
                        organism = Homo sapiens
SEQUENCE: 3
KVLEHVVRA                                                                  9

SEQ ID NO: 4            moltype = AA  length = 9
FEATURE                 Location/Qualifiers
source                  1..9
                        mol_type = protein
                        organism = Homo sapiens
SEQUENCE: 4
KVLEHVVRI                                                                  9

SEQ ID NO: 5            moltype = AA  length = 9
FEATURE                 Location/Qualifiers
source                  1..9
                        mol_type = protein
                        organism = Homo sapiens
SEQUENCE: 5
KLLEHVVRV                                                                  9

SEQ ID NO: 6            moltype = AA  length = 9
FEATURE                 Location/Qualifiers
source                  1..9
                        mol_type = protein
                        organism = Homo sapiens
SEQUENCE: 6
KLLEHVVRL                                                                  9

SEQ ID NO: 7            moltype = AA  length = 9
FEATURE                 Location/Qualifiers
source                  1..9
                        mol_type = protein
                        organism = Homo sapiens
SEQUENCE: 7
KLLEHVVRA                                                                  9

SEQ ID NO: 8            moltype = AA  length = 9
FEATURE                 Location/Qualifiers
source                  1..9
                        mol_type = protein
                        organism = Homo sapiens
SEQUENCE: 8
KLLEHVVRI                                                                  9

SEQ ID NO: 9            moltype = AA  length = 9
FEATURE                 Location/Qualifiers
source                  1..9
                        mol_type = protein
                        organism = Homo sapiens
SEQUENCE: 9
KALEHVVRV                                                                  9
```

-continued

| | | |
|---|---|---|
| SEQ ID NO: 10<br>FEATURE<br>source | moltype = AA   length = 9<br>Location/Qualifiers<br>1..9<br>mol_type = protein<br>organism = Homo sapiens | |
| SEQUENCE: 10<br>KALEHVVRL | | 9 |
| SEQ ID NO: 11<br>FEATURE<br>source | moltype = AA   length = 9<br>Location/Qualifiers<br>1..9<br>mol_type = protein<br>organism = Homo sapiens | |
| SEQUENCE: 11<br>KALEHVVRA | | 9 |
| SEQ ID NO: 12<br>FEATURE<br>source | moltype = AA   length = 9<br>Location/Qualifiers<br>1..9<br>mol_type = protein<br>organism = Homo sapiens | |
| SEQUENCE: 12<br>KALEHVVRI | | 9 |
| SEQ ID NO: 13<br>FEATURE<br>source | moltype = AA   length = 9<br>Location/Qualifiers<br>1..9<br>mol_type = protein<br>organism = Homo sapiens | |
| SEQUENCE: 13<br>YLLEHVVRV | | 9 |
| SEQ ID NO: 14<br>FEATURE<br>source | moltype = AA   length = 9<br>Location/Qualifiers<br>1..9<br>mol_type = protein<br>organism = Homo sapiens | |
| SEQUENCE: 14<br>YLLEHVVRL | | 9 |
| SEQ ID NO: 15<br>FEATURE<br>source | moltype = AA   length = 9<br>Location/Qualifiers<br>1..9<br>mol_type = protein<br>organism = Homo sapiens | |
| SEQUENCE: 15<br>YLLEHVVRA | | 9 |
| SEQ ID NO: 16<br>FEATURE<br>source | moltype = AA   length = 9<br>Location/Qualifiers<br>1..9<br>mol_type = protein<br>organism = Homo sapiens | |
| SEQUENCE: 16<br>YLLEHVVRI | | 9 |
| SEQ ID NO: 17<br>FEATURE<br>source | moltype = AA   length = 9<br>Location/Qualifiers<br>1..9<br>mol_type = protein<br>organism = Homo sapiens | |
| SEQUENCE: 17<br>YALEHVVRV | | 9 |
| SEQ ID NO: 18<br>FEATURE<br>source | moltype = AA   length = 9<br>Location/Qualifiers<br>1..9<br>mol_type = protein<br>organism = Homo sapiens | |
| SEQUENCE: 18<br>YALEHVVRL | | 9 |
| SEQ ID NO: 19<br>FEATURE<br>source | moltype = AA   length = 9<br>Location/Qualifiers<br>1..9<br>mol_type = protein<br>organism = Homo sapiens | |
| SEQUENCE: 19<br>YALEHVVRA | | 9 |

```
SEQ ID NO: 20              moltype = AA  length = 9
FEATURE                    Location/Qualifiers
source                     1..9
                           mol_type = protein
                           organism = Homo sapiens
SEQUENCE: 20
YALEHVVRI                                                                          9

SEQ ID NO: 21              moltype = AA  length = 9
FEATURE                    Location/Qualifiers
source                     1..9
                           mol_type = protein
                           organism = Homo sapiens
SEQUENCE: 21
YVLEHVVRV                                                                          9

SEQ ID NO: 22              moltype = AA  length = 9
FEATURE                    Location/Qualifiers
source                     1..9
                           mol_type = protein
                           organism = Homo sapiens
SEQUENCE: 22
YVLEHVVRL                                                                          9

SEQ ID NO: 23              moltype = AA  length = 9
FEATURE                    Location/Qualifiers
source                     1..9
                           mol_type = protein
                           organism = Homo sapiens
SEQUENCE: 23
YVLEHVVRA                                                                          9

SEQ ID NO: 24              moltype = AA  length = 9
FEATURE                    Location/Qualifiers
source                     1..9
                           mol_type = protein
                           organism = Homo sapiens
SEQUENCE: 24
YVLEHVVRI                                                                          9

SEQ ID NO: 25              moltype = AA  length = 9
FEATURE                    Location/Qualifiers
VARIANT                    1
                           note = Xaa can be Lys or Tyr
VARIANT                    2
                           note = Xaa can be Val, Leu, or Ala
VARIANT                    9
                           note = Xaa can be Val, Leu, Ala, or Ile
source                     1..9
                           mol_type = protein
                           organism = Homo sapiens
SEQUENCE: 25
XXLEHVVRX                                                                          9
```

What is claimed is:

1. A method of treating a patient who has hepatocellular cancer, comprising administering to said patient a population of activated T cells that kill cancer cells that present on the surface a peptide consisting of the amino acid sequence of KVLEHVVRV (SEQ ID NO: 1) wherein the activated T cells bind the peptide in a complex with an MHC class I molecule on the surface of the cancer cells.

2. The method of claim 1, wherein the activated T cells are cytotoxic T cells produced by transducing T cells with a T cell receptor (TCR) that binds the peptide in a complex with an MHC class I molecule on the surface of the cancer cells.

3. The method of claim 1, wherein the activated T cells are cytotoxic T cells produced by contacting T cells with an antigen presenting cell that expresses the peptide in a complex with an MHC class I molecule on the surface of the antigen presenting cell, for a period of time sufficient to activate said T cell.

4. The method of claim 1, further comprising administering to said patient at least one adjuvant selected from the group consisting of anti-CD40 antibody, imiquimod, resiquimod, GM-CSF, cyclophosphamide, sunitinib, bevacizumab, interferon-alpha, interferon-beta, CpG oligonucleotides, poly-(I:C), RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

5. The method of claim 4, wherein the at least one adjuvant is IL-2.

6. The method of claim 4, wherein the at least one adjuvant is IL-7.

7. The method of claim 4, wherein the at least one adjuvant is IL-15.

8. The method of claim 4, wherein the at least one adjuvant is IL-21.

9. The method of claim 4, wherein the at least one adjuvant is IL-1.

10. The method of claim 4, wherein the at least one adjuvant is IL-12.

11. A method of eliciting an immune response in a patient who has hepatocellular cancer, comprising administering to said patient a population of activated T cells that kill cancer cells that present on the surface a peptide consisting of the amino acid sequence of KVLEHVVRV (SEQ ID NO: 1) wherein the activated T cells bind the peptide in a complex with an MHC class I molecule on the surface of the cancer cells.

12. The method of claim 11, wherein the activated T cells are cytotoxic T cells produced by transducing T cells with a TCR that binds the peptide in a complex with an MHC class I molecule on the surface of the cancer cells.

13. The method of claim 11, wherein the activated T cells are cytotoxic T cells produced by contacting T cells with an antigen presenting cell that expresses the peptide in a complex with an MHC class I molecule on the surface of the antigen presenting cell, for a period of time sufficient to activate said T cell.

14. The method of claim 11, further comprising administering to said patient at least one adjuvant selected from the group consisting of anti-CD40 antibody, imiquimod, resiquimod, GM-CSF, cyclophosphamide, sunitinib, bevacizumab, interferon-alpha, interferon-beta, CpG oligonucleotides, poly-(I:C), RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

15. The method of claim 14, wherein the at least one adjuvant is IL-2.

16. The method of claim 14, wherein the at least one adjuvant is IL-7.

17. The method of claim 14, wherein the at least one adjuvant is IL-15.

18. The method of claim 14, wherein the at least one adjuvant is IL-21.

19. The method of claim 14, wherein the at least one adjuvant is IL-1.

20. The method of claim 14, wherein the at least one adjuvant is IL-12.

* * * * *